US010537565B2

(12) United States Patent
Hurter et al.

(10) Patent No.: US 10,537,565 B2
(45) Date of Patent: Jan. 21, 2020

(54) SOLID FORMS OF N-[2,4-BIS(1,1-DIMETHYLETHYL)-5-HYDROXYPHENYL]-1,4-DIHYDRO-4-OXOQUINOLINE-3-CARBOXAMIDE

(71) Applicant: Vertex Pharmaceuticals Incorporated, Boston, MA (US)

(72) Inventors: Patricia Hurter, Harvard, MA (US); William Rowe, Medford, MA (US); Christopher R. Young, Waltham, MA (US); Adriana Costache, Cambridge, MA (US); Patrick R. Connelly, Harvard, MA (US); Mariusz Krawiec, Marlborough, MA (US); Yuchuan Gong, Waukegan, IL (US); Yushi Feng, Zionsville, IN (US); Martin Trudeau, Shannon (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/900,147

(22) Filed: Feb. 20, 2018

(65) Prior Publication Data

US 2019/0070162 A1 Mar. 7, 2019

Related U.S. Application Data

(63) Continuation of application No. 15/584,324, filed on May 2, 2017, now Pat. No. 9,931,334, which is a continuation of application No. 14/852,892, filed on Sep. 14, 2015, now Pat. No. 9,670,163, which is a continuation of application No. 14/272,692, filed on May 8, 2014, now Pat. No. 9,139,530, which is a continuation of application No. 13/785,692, filed on Mar. 5, 2013, now Pat. No. 8,754,224, which is a continuation of application No. 13/358,778, filed on Jan. 26, 2012, now Pat. No. 8,410,274, which is a continuation of application No. 11/647,505, filed on Dec. 28, 2006, now abandoned.

(60) Provisional application No. 60/754,381, filed on Dec. 28, 2005.

(51) Int. Cl.
C07D 215/56 (2006.01)
A61K 31/47 (2006.01)

(52) U.S. Cl.
CPC ............ *A61K 31/47* (2013.01); *C07D 215/56* (2013.01); *A61K 2300/00* (2013.01); *C07B 2200/13* (2013.01); *Y10T 428/2982* (2015.01)

(58) Field of Classification Search
CPC .............. A61K 31/47; C07D 215/56
See application file for complete search history.

(56) References Cited

U.S. PATENT DOCUMENTS

| | | |
|---|---|---|
| 3,443,940 A | 5/1969 | Bloom et al. |
| 3,524,858 A | 8/1970 | Kaminsky et al. |
| 3,698,292 A | 10/1972 | Koester |
| 3,812,094 A | 5/1974 | MacLeay et al. |
| 3,931,145 A | 1/1976 | Stanley et al. |
| 3,992,540 A | 11/1976 | Clemence et al. |
| 4,107,310 A | 8/1978 | Allais et al. |
| 4,110,355 A | 8/1978 | Bloom et al. |
| 4,221,779 A | 9/1980 | Graham |
| 4,284,629 A | 8/1981 | Grohe et al. |
| 4,312,870 A | 1/1982 | Yokoyama |
| 4,450,166 A | 5/1984 | Clemence et al. |
| 4,450,167 A | 5/1984 | Le Martret et al. |
| 4,638,067 A | 1/1987 | Culbertson et al. |
| 4,777,252 A | 10/1988 | Slusarchyk et al. |
| 4,786,644 A | 11/1988 | Glamkowski et al. |
| 4,845,105 A | 7/1989 | Clemence et al. |
| 4,908,366 A | 3/1990 | Schriewer et al. |
| 4,956,465 A | 9/1990 | Schriewer et al. |
| 5,026,711 A | 6/1991 | Mendes et al. |
| 5,175,151 A | 12/1992 | Afonso et al. |
| 5,180,400 A | 1/1993 | Baudry et al. |
| 5,254,135 A | 10/1993 | Lang et al. |
| 5,281,612 A | 1/1994 | Domagala et al. |
| 5,322,847 A | 6/1994 | Marfat et al. |
| 5,352,690 A | 10/1994 | Sofia |
| 5,364,414 A | 11/1994 | Lang et al. |
| 5,378,694 A | 1/1995 | Afonso et al. |
| 5,380,713 A | 1/1995 | Balasubramanian et al. |
| 5,409,503 A | 4/1995 | Clausen et al. |
| 5,412,104 A | 5/1995 | Afonso et al. |
| 5,491,139 A | 2/1996 | Demuth, Jr. et al. |
| 5,527,763 A | 6/1996 | Miyazaki et al. |
| 5,536,727 A | 7/1996 | Witzel et al. |

(Continued)

FOREIGN PATENT DOCUMENTS

| CA | 1025856 A1 | 2/1978 |
|---|---|---|
| CA | 2065106 A1 | 10/1992 |

(Continued)

OTHER PUBLICATIONS

Accurso, F. J. et al. (2009) "Final results of a 14- and 28-day study of VX-770 in subjects with CF" *J. Cystic Fibrosis*, vol. 8, Supplement 2, Abstracts of the 32nd European Cystic Fibrosis Conference, Jun. 10-13, 2009, Abstract 97, p. S25.

Akama, T. et al. (Jun. 1997) "Design and synthesis of potent antitumor 5,4'-diaminoflavone derivatives based on metabolic considerations" *J Med Chem*, 40(12):1894-1900.

American College of Chest Physicians (2004) *Living Well With COPD: Chronic Bronchitis and Emphysema. Patient Education Guide.* Northbrook, IL, USA; Product Code: 5032, 44 pages.

(Continued)

*Primary Examiner* — D Margaret M Seaman
(74) *Attorney, Agent, or Firm* — Finnegan, Henderson, Farabow, Garrett & Dunner, LLP

(57) ABSTRACT

The present invention relates to solid state forms of N-[2,4-bis(1,1-dimethylethyl)-5-hydroxyphenyl]-1,4-dihydro-4-oxoquinoline-3-carboxamide (Compound 1), pharmaceutical compositions thereof and methods therewith.

26 Claims, 12 Drawing Sheets

(56) References Cited

U.S. PATENT DOCUMENTS

| | | |
|---|---|---|
| 5,573,868 A | 11/1996 | Umemoto et al. |
| 5,610,162 A | 3/1997 | Witzel et al. |
| 5,663,179 A | 9/1997 | Dumaitre et al. |
| 5,708,000 A | 1/1998 | Charvet-Faury et al. |
| 5,728,691 A | 3/1998 | Corpi Constantino |
| 5,744,471 A | 4/1998 | Bare et al. |
| 5,750,754 A | 5/1998 | Mills |
| 5,753,666 A | 5/1998 | Beasley et al. |
| 5,804,588 A | 9/1998 | Dyke et al. |
| 5,807,869 A | 9/1998 | Furuya et al. |
| 5,811,553 A | 9/1998 | Farina et al. |
| 5,834,485 A | 11/1998 | Dyke et al. |
| 5,840,745 A | 11/1998 | Buzzetti et al. |
| 5,874,424 A | 2/1999 | Batchelor et al. |
| 5,891,878 A | 4/1999 | Beasley et al. |
| 5,892,114 A | 4/1999 | Goldmann et al. |
| 5,938,792 A | 8/1999 | Lang et al. |
| 5,948,814 A | 9/1999 | Hwang et al. |
| 6,039,974 A | 3/2000 | MacLaren et al. |
| 6,069,151 A | 5/2000 | Dyke et al. |
| 6,133,265 A | 10/2000 | Blum et al. |
| 6,194,454 B1 | 2/2001 | Dow |
| 6,215,016 B1 | 4/2001 | Kawai et al. |
| 6,218,393 B1 | 4/2001 | Ryder et al. |
| 6,258,822 B1 | 7/2001 | Geyer et al. |
| 6,316,617 B1 | 11/2001 | Blum et al. |
| 6,362,340 B1 | 3/2002 | Dang |
| 6,395,750 B1 | 5/2002 | Hedlund et al. |
| 6,413,956 B1 | 7/2002 | Albaugh et al. |
| 6,429,207 B1 | 8/2002 | Van Wagenen et al. |
| 6,444,617 B1 | 9/2002 | Takaishi et al. |
| 6,448,254 B1 | 9/2002 | Lubisch et al. |
| 6,515,001 B2 | 2/2003 | Saxena et al. |
| 6,544,987 B2 | 4/2003 | Guo et al. |
| 6,720,344 B2 | 4/2004 | Kerwin et al. |
| 6,723,850 B1 | 4/2004 | Guarna et al. |
| 6,790,858 B2 | 9/2004 | Strehlke et al. |
| 6,849,648 B2 | 2/2005 | Bunker et al. |
| 6,878,713 B2 | 4/2005 | De Souza et al. |
| 6,930,131 B2 | 8/2005 | Sabatucci et al. |
| 6,974,806 B2 | 12/2005 | Terashita et al. |
| 6,977,001 B2 | 12/2005 | Sauter et al. |
| 7,001,770 B1 | 2/2006 | Atencio et al. |
| 7,037,913 B2 | 5/2006 | Wang et al. |
| 7,084,156 B2 | 8/2006 | DeVita et al. |
| 7,105,535 B2 | 9/2006 | Berta et al. |
| 7,112,594 B2 | 9/2006 | Ushio et al. |
| 7,179,839 B2 | 2/2007 | Strobel et al. |
| 7,223,759 B2 | 5/2007 | Zhou et al. |
| 7,407,976 B2 | 8/2008 | Miller et al. |
| 7,495,103 B2 | 2/2009 | Hadida Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,939,558 B2 | 5/2011 | Verkman et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,518,441 B2 | 8/2013 | Higuchi et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |

(56) References Cited

U.S. PATENT DOCUMENTS

| | | |
|---|---|---|
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 * | 9/2015 | Hurter .................. C07D 215/56 |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |
| 9,732,080 B2 | 8/2017 | Hadida-Ruah et al. |
| 9,751,839 B2 | 9/2017 | Demattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,840,499 B2 | 12/2017 | Keshavarz-Shokri et al. |
| 9,931,334 B2 | 4/2018 | Hurter et al. |
| 9,974,781 B2 | 5/2018 | Hadida Ruah et al. |
| 10,022,352 B2 | 7/2018 | Hadida Ruah et al. |
| 10,058,546 B2 | 8/2018 | Alargova et al. |
| 10,071,979 B2 | 9/2018 | Tanoury et al. |
| 10,076,513 B2 | 9/2018 | Verwijs et al. |
| 10,081,621 B2 | 9/2018 | Keshavarz-Shokri et al. |
| 10,206,877 B2 | 2/2019 | Phenix et al. |
| 10,239,867 B2 | 3/2019 | Hadida Ruah et al. |
| 2002/0173520 A1 | 11/2002 | Bjork et al. |
| 2003/0100501 A1 | 5/2003 | Davis et al. |
| 2003/0195191 A1 | 10/2003 | Burton et al. |
| 2003/0195201 A1 | 10/2003 | Bo et al. |
| 2004/0033959 A1 | 2/2004 | Chen et al. |
| 2004/0043983 A1 | 3/2004 | Li |
| 2004/0082798 A1 | 4/2004 | Alonso-Alija et al. |
| 2004/0121005 A1 | 6/2004 | Altreuter et al. |
| 2005/0059035 A1 | 3/2005 | Huang et al. |
| 2005/0113423 A1 | 5/2005 | Van Goor et al. |
| 2005/0147669 A1 | 7/2005 | Lawrence et al. |
| 2005/0176741 A1 | 8/2005 | Okano et al. |
| 2005/0181041 A1 | 8/2005 | Goldman |
| 2005/0186261 A1 | 8/2005 | Avelar et al. |
| 2005/0187300 A1 | 8/2005 | Bajji et al. |
| 2005/0192315 A1 | 9/2005 | Jansson et al. |
| 2005/0208095 A1 | 9/2005 | Hunter et al. |
| 2005/0222199 A1 | 10/2005 | Hayman et al. |
| 2006/0003005 A1 | 1/2006 | Cao et al. |
| 2006/0148806 A1 | 7/2006 | Watanuki et al. |
| 2006/0178516 A1 | 8/2006 | Johnstone et al. |
| 2008/0317853 A1 | 12/2008 | Kashid et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2009/0274756 A1 | 11/2009 | Ukai et al. |
| 2009/0285887 A1 | 11/2009 | Abu-Baker et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Doukou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0094499 A1 | 4/2014 | Alargova et al. |
| 2014/0112988 A1 | 4/2014 | Rowe et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0150879 A2 | 6/2015 | Van Goor et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0218122 A1 | 8/2015 | Tanoury et al. |

(56) References Cited

U.S. PATENT DOCUMENTS

| | | |
|---|---|---|
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0095858 A1 | 4/2016 | Miller et al. |
| 2016/0143898 A1 | 5/2016 | Hadida Ruah et al. |
| 2016/0166540 A1 | 6/2016 | Looker et al. |
| 2016/0221952 A1 | 8/2016 | Yang et al. |
| 2016/0228414 A1 | 8/2016 | Hadida Ruah et al. |
| 2016/0237079 A1 | 8/2016 | Hadida Ruah et al. |
| 2016/0271105 A1 | 9/2016 | Hadida Ruah et al. |
| 2016/0303096 A1 | 10/2016 | Verwijs et al. |
| 2016/0318931 A1 | 11/2016 | Hadida Ruah et al. |
| 2016/0324788 A1 | 11/2016 | Verwijs |
| 2016/0324846 A1 | 11/2016 | Verwijs et al. |
| 2016/0354316 A1 | 12/2016 | Swinney et al. |
| 2017/0087144 A1 | 3/2017 | Rowe et al. |
| 2017/0100340 A1 | 4/2017 | Dokou et al. |
| 2017/0107205 A1 | 4/2017 | Hadida Ruah et al. |
| 2017/0107206 A1 | 4/2017 | Hadida Ruah et al. |
| 2017/0266176 A1 | 9/2017 | Alargova et al. |
| 2018/0008546 A1 | 1/2018 | Verwijs et al. |
| 2018/0127398 A1 | 5/2018 | Keshavarz-Shokri et al. |
| 2018/0153874 A1 | 6/2018 | Van Goor et al. |
| 2018/0280349 A1 | 10/2018 | Van Goor et al. |
| 2019/0038615 A1 | 2/2019 | Van Goor et al. |
| 2019/0070162 A1 | 3/2019 | Hurter et al. |
| 2019/0076419 A1 | 3/2019 | Hadida Ruah et al. |
| 2019/0125674 A1 | 5/2019 | Phenix et al. |
| 2019/0144450 A1 | 5/2019 | Hadida Ruah et al. |

FOREIGN PATENT DOCUMENTS

| | | |
|---|---|---|
| CA | 2571949 A | 1/2006 |
| CA | 2769695 A1 | 2/2011 |
| CN | 1473827 A | 2/2004 |
| CN | 101006076 A | 7/2007 |
| CN | 101287732 A | 10/2008 |
| CN | 101374849 A | 2/2009 |
| CN | 101384172 A | 3/2009 |
| CN | 101460489 A | 6/2009 |
| CN | 105884628 A | 8/2016 |
| DE | 2050966 A1 | 4/1971 |
| DE | 2407744 A1 | 8/1974 |
| DE | 2415763 A1 | 10/1974 |
| DE | 3827253 A1 | 3/1989 |
| DE | 279887 A1 | 6/1990 |
| DE | 3903799 A1 | 8/1990 |
| DE | 4017516 A1 | 12/1991 |
| DE | 19601142 A1 | 1/1997 |
| DE | 19532235 A1 | 3/1997 |
| EA | 003945 B1 | 10/2003 |
| EA | 004043 B1 | 12/2003 |
| EP | 0004279 B1 | 12/1982 |
| EP | 0308702 A2 | 3/1989 |
| EP | 0332033 A2 | 9/1989 |
| EP | 0332930 A2 | 9/1989 |
| EP | 0343398 A2 | 11/1989 |
| EP | 0382034 A1 | 1/1990 |
| EP | 0363585 A1 | 4/1990 |
| EP | 0409025 A2 | 1/1991 |
| EP | 0425345 A1 | 5/1991 |
| EP | 0460996 A1 | 12/1991 |
| EP | 0472091 B1 | 11/1994 |
| EP | 0705835 A1 | 4/1996 |
| EP | 1227084 B1 | 12/2005 |
| EP | 1224172 B1 | 4/2007 |
| EP | 0901786 B1 | 6/2007 |
| EP | 3034497 A1 | 6/2016 |
| FR | 960299 A | 4/1950 |
| FR | 2002888 A1 | 10/1969 |
| FR | 2324304 A2 | 4/1977 |
| FR | 2340092 A2 | 9/1977 |
| FR | 2537140 A1 | 6/1984 |
| GB | 1433774 A | 4/1976 |
| GB | 2372986 A | 9/2002 |
| IN | 5333/CHE/2015 | 7/2016 |
| JP | 50-24296 A | 3/1975 |
| JP | 50-29574 A | 3/1975 |
| JP | 55-81878 A | 6/1980 |
| JP | 56-110612 A | 9/1981 |
| JP | 58-18361 A | 2/1983 |
| JP | 1-287066 A | 11/1989 |
| JP | 2-138260 A | 5/1990 |
| JP | 3-34977 A | 2/1991 |
| JP | 3-193725 A | 8/1991 |
| JP | 6-72979 A | 3/1994 |
| JP | 6-509061 A | 10/1994 |
| JP | 7-33729 A | 2/1995 |
| JP | 7-82498 A | 3/1995 |
| JP | 7-179407 A | 7/1995 |
| JP | 8-301849 A | 11/1996 |
| JP | 9-71534 A | 3/1997 |
| JP | 11-116502 A | 4/1999 |
| JP | 11-513021 A | 9/1999 |
| JP | 2000-16982 A | 1/2000 |
| JP | 2000-505450 A | 5/2000 |
| JP | 2000-256358 A | 9/2000 |
| JP | 2001-502683 A | 2/2001 |
| JP | 2001-199965 A | 7/2001 |
| JP | 2001-233859 A | 8/2001 |
| JP | 2002-212179 A | 7/2002 |
| JP | 2002-322054 A | 11/2002 |
| JP | 2002-322154 A | 11/2002 |
| JP | 2002-326935 A | 11/2002 |
| JP | 2003-12667 A | 1/2003 |
| JP | 2003-238413 A | 8/2003 |
| JP | 2004-189738 A | 7/2004 |
| JP | 2004-532209 A | 10/2004 |
| JP | 2005-533770 A | 11/2005 |
| JP | 2006-206612 A | 8/2006 |
| JP | 2008-504291 A | 2/2008 |
| JP | 2009-522278 A | 6/2009 |
| JP | 2012-107069 A | 6/2012 |
| JP | 4947658 B2 | 6/2012 |
| JP | 2013-173750 A | 9/2013 |
| MX | MX/a/2013/002353 | 9/2013 |
| RU | 2047614 C1 | 11/1995 |
| RU | 2155754 C2 | 9/2000 |
| RU | 2270186 C2 | 2/2006 |
| RU | 2389495 C2 | 10/2008 |
| SU | 1360584 A3 | 12/1987 |
| SU | 1779243 A3 | 11/1992 |
| SU | 1796623 A1 | 2/1993 |
| WO | WO 1991/05783 A1 | 5/1991 |
| WO | WO 1992/14714 A1 | 9/1992 |
| WO | WO 1992/18093 A1 | 10/1992 |
| WO | WO 1992/18483 A1 | 10/1992 |
| WO | WO 1994/14797 A1 | 7/1994 |
| WO | WO 1995/11244 A1 | 4/1995 |
| WO | WO 1995/32948 A1 | 12/1995 |
| WO | WO 1996/15099 A1 | 5/1996 |
| WO | WO 1996/19239 A1 | 6/1996 |
| WO | WO 1997/04779 A1 | 2/1997 |
| WO | WO 1997/23462 A1 | 7/1997 |
| WO | WO 1997/30999 A1 | 8/1997 |
| WO | WO 1998/17648 A1 | 4/1998 |
| WO | WO 1998/026127 A1 | 6/1998 |
| WO | WO 1998/031226 A1 | 7/1998 |
| WO | WO 1999/05096 A2 | 2/1999 |
| WO | WO 1999/32436 A1 | 7/1999 |
| WO | WO 1999/46237 A1 | 9/1999 |
| WO | WO 1999/46267 A1 | 9/1999 |
| WO | WO 2000/40561 A1 | 7/2000 |
| WO | WO 2000/68202 A1 | 11/2000 |
| WO | WO 2001/21159 A2 | 3/2001 |
| WO | WO 2001/30757 A1 | 5/2001 |
| WO | WO 2001/34570 A1 | 5/2001 |
| WO | WO 2001/40217 A1 | 6/2001 |

(56) References Cited

FOREIGN PATENT DOCUMENTS

| | | |
|---|---|---|
| WO | WO 2001/47924 A1 | 7/2001 |
| WO | WO 2001/87806 A2 | 11/2001 |
| WO | WO 2002/003938 A1 | 1/2002 |
| WO | WO 2002/038126 A2 | 5/2002 |
| WO | WO 2002/078693 A2 | 10/2002 |
| WO | WO 2002/094809 A1 | 11/2002 |
| WO | WO 2003/043992 A1 | 5/2003 |
| WO | WO 2003/063821 A2 | 8/2003 |
| WO | WO 2003/101454 A1 | 12/2003 |
| WO | WO 2004/039783 A1 | 5/2004 |
| WO | WO 2004/048314 A1 | 6/2004 |
| WO | WO 2004/105779 A2 | 12/2004 |
| WO | WO 2005/035514 A2 | 4/2005 |
| WO | WO 2005/046696 A1 | 5/2005 |
| WO | WO 2005/049018 A1 | 6/2005 |
| WO | WO 2005/075435 A1 | 8/2005 |
| WO | WO 2005/094805 A1 | 10/2005 |
| WO | WO 2005/120497 A2 | 12/2005 |
| WO | WO 2006/002421 A2 | 1/2006 |
| WO | WO 2006/034420 A2 | 3/2006 |
| WO | WO 2006/101740 A2 | 9/2006 |
| WO | WO 2006/127588 A2 | 11/2006 |
| WO | WO 2007/021982 A2 | 2/2007 |
| WO | WO 2007/056341 A1 | 5/2007 |
| WO | WO 2007/067559 A2 | 6/2007 |
| WO | WO 2007/075901 A2 | 7/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/106537 A2 | 9/2007 |
| WO | WO 2007/106960 A1 | 9/2007 |
| WO | WO 2007/117715 A2 | 10/2007 |
| WO | WO 2007/124318 A1 | 11/2007 |
| WO | WO 2007/134279 A2 | 11/2007 |
| WO | WO 2008/083130 A2 | 7/2008 |
| WO | WO 2008/127399 A2 | 10/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/073757 A1 | 6/2009 |
| WO | WO 2009/076141 A2 | 6/2009 |
| WO | WO 2009/076593 A1 | 6/2009 |
| WO | WO 2010/019239 A2 | 2/2010 |
| WO | WO 2010/025126 A1 | 3/2010 |
| WO | WO 2010/037066 A2 | 4/2010 |
| WO | WO 2010/048526 A2 | 4/2010 |
| WO | WO 2010/048564 A1 | 4/2010 |
| WO | WO 2010/048573 A1 | 4/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/133951 A1 | 10/2011 |
| WO | WO 2011/133953 A1 | 10/2011 |
| WO | WO 2011/146901 A1 | 11/2011 |
| WO | WO 2011/163614 A2 | 12/2011 |
| WO | WO 2012/027247 A2 | 3/2012 |
| WO | WO 2012/027731 A2 | 3/2012 |
| WO | WO 2013/067410 A1 | 5/2013 |
| WO | WO 2013/185112 A1 | 12/2013 |
| WO | WO 2014/014841 A1 | 1/2014 |
| WO | WO 2016/086103 A1 | 6/2016 |
| WO | WO 2016/086136 A1 | 6/2016 |
| WO | WO 2016/087665 A2 | 6/2016 |
| WO | WO 2016/092561 A2 | 6/2016 |
| WO | WO 2016/160945 A1 | 10/2016 |
| WO | WO 2016/180784 A1 | 11/2016 |
| WO | WO 2016/181414 A1 | 11/2016 |
| WO | WO 2016/185423 A1 | 11/2016 |
| WO | WO 2016/199085 A1 | 12/2016 |

OTHER PUBLICATIONS

Archimica (Oct. 2006) *Coupling Agent® T3P—The Water Scavenger. High-Performance Amide/Peptide Bond Formations, Dehydrations and Condensations.* [online] Retrieved Apr. 11, 2011, from the Internet: http://www.archimica.com/PDF/ARCHIMICA_T3P_Brochure.pdf (20 pages).

Ashizawa, K. (2002) *Polymorphism and Crystallization of the Pharmaceutical Drugs*, pp. 273, 278, 305-317 (Japanese).

Aulton, M.E. (Ed.) (2002) *Pharmaceutics: The Science of Dosage Design.* 2nd Ed. Churchill Livingston; pp. 304-321.

Berge, S.M. et al. (1977) "Pharmaceutical Salts" *J Pharmac Sci*, 66(1):1-19.

Bernstein, J. et al. (1995) "Patterns in Hydrogen Bonding: Functionality and Graph Set Analysis in Crystals" *Angew Chem Int Ed Engl*, 34:1555-1573.

Bombeiri, C. et al. (1998) "Complete mutational screening of the CFTR gene in 120 patients with pulmonary disease" *Human Genet*, 103:718-722.

Bombeiri, C. et al. (2011) "Recommendations for the classification of diseases as CFTR-related disorders" *J Cyst Fibros*, 10(suppl. 2):S86-S102.

Brittain, H. (Jul. 2001) "X-ray Diffraction III: Pharmaceutical Applications of X-ray Powder Diffraction" *Spectroscopy*, 16(7):14-18.

Brittain, H.G. (Apr. 1997) "Spectral Methods for the Characterization of Polymorphs and Solvates" *J Pharm Sci*, 86(4):405-412.

Brown, R.K. et al. (1954) "6-Aminoindole" *J Am. Chem Soc*, 76(20):5149-5150.

Brown, R.K. et al. (1955) "Derivatives of Indole, 6-Amino-3-indoleacetic Acid" *J Am Chem Soc*, 77(14):3839-3842.

Brown, R.K. et al. (1956) "Some Indole Derivatives Tested for Antitubercular Activity" *J Org Chem*, 21:261-262.

Burvall, K.M. et al. (2002) "The tyrosine kinase inhibitor genistein increases basal cAMP and potentiates forskolin-induced cAMP accumulation in A549 human airway epithelial cells" *Mol Cell Biol*, 240:131-133.

Byrn, S. et al. (1995) "Pharmaceutical Solids: A Strategic Approach to Regulatory Considerations" *Pharmaceutical Research*, 12(7):945-954.

Cai, Z-W. et al. (2011) "Targeting F508del-CFTR to develop rational new therapies for cystic fibrosis" *Acta Pharmacologica Sinica*, 32(6):693-701.

Caira, M.R. (Jan. 1, 1998) "Crystalline Polymorphism of Organic Compounds" *Topics in Chemistry*, 198:163-208.

Carta, A. et al. (2003) "Synthesis and Biological Evaluation of Triazolo[4,5-g]Quinolines, Imidazo[4,5-g]Quinolines and Pyriodo[2,3-g]Quinoxalines. Part II" *Heterocycles*, 60(4):833-842.

Chemical Abstracts Service, 'Registry' File, RN 174311-74-1. STN Database [online]. Entry Date: Mar. 19, 1996, retrieved on Apr. 25, 2013.

Chemical Abstracts Service, 'Registry' File, RN 325779-54-2. STN Database [online]. Entry Date: Mar. 6, 2001, retrieved on Jan. 28, 2016.

Chemical Abstracts Service, 'Registry' File, RN 329691-97-6. STN Database [online]. Entry Date: Apr. 2, 2001, retrieved on Jan. 28, 2016.

Chemical Abstracts Service, 'Registry' File, RN 329691-99-8. STN Database [online]. Entry Date: Apr. 2, 2001, retrieved on Jan. 28, 2016.

Chemical Abstracts Service, 'Registry' File, RN 329692-01-5. STN Database [online]. Entry Date: Apr. 2, 2001, retrieved on Jan. 28, 2016.

Chemical Abstracts Service, 'Registry' File, RN 329692-03-7. STN Database [online]. Entry Date: Apr. 2, 2001, retrieved on Jan. 28, 2016.

Chemical Abstracts Service, 'Registry' File, RN 329692-05-9. STN Database [online]. Entry Date: Apr. 2, 2001, retrieved on Jan. 28, 2016.

Chemical Abstracts Service, 'Registry' File, RN 329692-14-0. STN Database [online]. Entry Date: Apr. 2, 2001, retrieved on Jan. 28, 2016.

(56) References Cited

OTHER PUBLICATIONS

Chemical Abstracts Service, 'Registry' File, RN 625115-91-5. STN Database [online]. Entry Date: Dec. 9, 2003, retrieved on Apr. 25, 2013.
Chemical Abstracts Service, 'Registry' File, RN 629662-49-3. STN Database [online]. Entry Date: Dec. 22, 2003, retrieved on Jul. 24, 2015.
Chemical Abstracts Service, 'Registry' File, RN 849644-14-0; STN Database SciFinder® [online]. Entry Date: Nov. 2, 2004, retrieved on Mar. 25, 2014.
Clunes, M.T. et al. (2008) "Front-runners for pharmacotherapeutic correction of the airway ion transport defect in cystic fibrosis" *Current Opinion in Pharmacology*, 8(3):292-299.
Collawn, J.F. et al. (2010) "Targets for cystic fibrosis therapy: proteomic analysis and correction of mutant cystic fibrosis transmembrane conductance regulator" *Expert Review of Proteomics*, 7(4):495-506.
Cuthbert, A.W. (2010) "New horizons in the treatment of cystic fibrosis" *Br J Pharmacol*, 163:173-183.
De Meeus, A. et al. (1998) "Genetic Findings in Congenital Bilateral Aplasia of Vas Deferens Patients and Identification of Six Novel Mutations" *Human Mutation, Mutation in Brief*, #138 [online]. DOI: 10.1002/(SICI)1098-1004(1998)11:6<480::AID-HUMU10>3.0.CO;2-2, 10 pages. Final publication in vol. 11(6), p. 480.
Dhar, T.G. M. et al. (2003) "3-Cyanoindole-based Inhibitors of Inosine Monophosphate Dehydrogenase: Synthesis and Initial Structure-Activity Relationships" *Bioorg. Med. Chem. Lett.*, 13(20):3557-3560.
Dif, F. et al. (2004) "Severe osteopenia in CFTR-null mice" *Bone*, 35:595-603.
Dohmori, R. et al. (1976) "Synthetic Chemotherapeutic Agents. I. Synthesis of 2-Substituted Thiazolo[5,4-f]quinoline Derivatives" *Chem Pharm Bull*, 24:130-135.
Eckford, P.D.W. et al. (2012) "Cystic Fibrosis Transmembrane Conductance Regulator (CFTR) Potentiator VX-770 (Ivacaftor) Opens the Defective Channel Gate of Mutant CFTR in a Phosphorylation-dependent but ATP-independent Manner" *J Biol Chem*, 287(44):36639-36649.
Erlinger, S. (2011) "Molecular repair of a defective CFTR protein in cystic fibrosis" *Clinics and Research in Hepatology and Gastroenterology*, 35:254-256.
Ferec, C. et al. (2012) "Assessing the Disease-Liability of Mutations in CFTR" *Cold Spring Harbor Perspect Med*, 2:a009480 (13 pages).
Flume, P. A. et al. (2012) "Ivacaftor in Subjects With Cystic Fibrosis Who Are Homozygous for the F508del-CFTR Mutation" *Chest*, 142:718-724.
Galietta, L.J.V. et al. (2001) "Novel CFTR Chloride Channel Activators Identified by Screening of Combinatorial Libraries Based on Flavone and Benzoquinolizinium Lead Compounds" *J Biol Chem*, 276(23):19723-19728.
Grant, D.J.W. (1999) "Theory and Origin of Polymorphism" in *Polymorphism in Pharmaceutical Solids*, H.G. Brittain, Ed.; Ch.1, pp. 1-10.
Grohe, K. et al. (1987) "Synthese von 1-amino-4-chinolon-3-carbonsauren" *Liebigs Annalen Der Chemie*, 10:871-879.
Guillory, J.K. (1999) "Generation of Polymorphs, Hydrates, Solvates, and Amorphous Solids" in *Polymorphism in Pharmaceutical Solids*. H.G. Brittain, Ed.; Ch.5, pp. 183-226.
Guo, J-H. (2004 Jun) "Lactose in Pharmaceutical Applications" *Drug Delivery*, vol. 4, No. 5 (7 pages).
Hama, T. et al. (2003) "Palladium-Catalyzed α-Arylation of Esters and Amides under More Neutral Conditions" *J Am Chem Soc*, 125(37):11176-11177.
Hancock, B.C. et al. (2000) "What is the True Solubility Advantage for Amorphous Pharmaceuticals?" *Pharmaceutical Research*, 17(4):397-404.
*Handbook for Preparing Crystal of Organic Compound—Principle and Know-how*, Maruzen Co., Ltd.: Jul. 25, 2008, pp. 57-84 (Japanese).

Hansen, K.T. et al. (Aug. 1991) "Carbamate ester prodrugs of dopaminergic compounds: synthesis, stability, and bioconversion" *J Pharm Sci*, 80(8):793-798.
Haynes, R.K. et al. (1972) "Amine Oxidation and the Chemistry of Quinone Imines. Part I. 3-Methoxy-4-t-butylaniline" *J Chem Soc, Perkins Trans*, 1:396-408.
Heilbron, I.M. et al. (1928) "The Intermolecular Condensation of Acetylmethylanthranilic Acid by Means of Phosphorus Pentachloride and the Formation of a Complex isoCyanine Dye" *J Chem Soc*, pp. 934-941.
Hennequin, L.F. et al. (1999) "Design and Structure-Activity Relationship of a New Class of Potent VEGF Receptor Tyrosine Kinase Inhibitors" *J Med Chem*, 42(26):5369-5389.
Hester, J.B. et al. (1964) "Enzyme Inhibitory Activity of 3-(2-Aminobutyl)indole Derivatives" *J Med Chem*, 7(3):274-279.
Hoffman, H.E. et al. (2005) "Allele-Specific Inhibitors of Protein Tyrosine Phosphatases" *J Am Chem Soc*, 127(9):2824-2825.
Imanishi, T. et al. (1996) "Evidence that a Hybrid Molecule of Norfloxacin and Biphenylacetic Acid is a Potent Antagonist at the GABAA Receptor" *Neuropharmacology*, 35(9/10):1271-1277.
International Patent Application No. PCT/US2005/022768, filed Jun. 24, 2005, by Vertex Pharmaceuticals Incorporated: International Search Report and Written Opinion, dated Jul. 25, 2006.
International Patent Application No. PCT/US2006/048810, filed Dec. 21, 2006, by Vertex Pharmaceuticals Incorporated: International Search Report and Written Opinion, dated Jul. 26, 2007.
International Patent Application No. PCT/US2006/048900, filed Dec. 21, 2006, by Vertex Pharmaceuticals Incorporated: International Search Report and Written Opinion, dated May 25, 2007.
International Patent Application No. PCT/US2006/049421, filed Dec. 28, 2006, by Vertex Pharmaceuticals, Inc.: International Search Report and Written Opinion, dated Sep. 25, 2007.
International Patent Application No. PCT/US2007/068857, filed May 14, 2007, by Vertex Pharmaceuticals Incorporated: International Search Report and Written Opinion, dated Sep. 9, 2008.
International Patent Application No. PCT/US2008/010728, filed Sep. 15, 2008, by Vertex Pharmaceuticals Incorporated: International Search Report and Written Opinion, dated Jul. 14, 2010.
International Patent Application No. PCT/US2009/004629, filed Aug. 13, 2009, by Vertex Pharmaceuticals Incorporated: International Search Report and Written Opinion, dated Mar. 24, 2011.
International Patent Application No. PCT/US2010/024609, filed Feb. 18, 2010, by Vertex Pharmaceuticals Incorporated: International Search Report and Written Opinion, dated Jun. 1, 2010.
International Patent Application No. PCT/US2010/028062, filed Mar. 19, 2010, by Vertex Pharmaceuticals Incorporated: International Search Report and Written Opinion, dated May 27, 2010.
International Patent Application No. PCT/US2010/028069, filed Mar. 19, 2010, by Vertex Pharmaceuticals Incorporated: International Search Report and Written Opinion, dated Aug. 25, 2010.
International Patent Application No. PCT/US2010/059920, filed Dec. 10, 2010, by Vertex Pharmaceuticals Incorporated: International Search Report and Written Opinion, dated Feb. 3, 2011.
International Patent Application No. PCT/US2011/029276, filed Mar. 21, 2011, by Vertex Pharmaceuticals Incorporated: International Search Report and Written Opinion, dated May 11, 2011.
International Patent Application No. PCT/US2011/033687, filed Apr. 22, 2011, by Vertex Pharmaceuticals Incorporated: International Search Report and Written Opinion, dated Aug. 30, 2011.
International Patent Application No. PCT/US2011/033689, filed Apr. 22, 2011, by Vertex Pharmaceuticals Incorporated: International Search Report and Written Opinion, dated Aug. 30, 2011.
International Patent Application No. PCT/US2011/033693, filed Apr. 22, 2011, by Vertex Pharmaceuticals Incorporated: International Search Report and Written Opinion, dated Aug. 30, 2011.
International Patent Application No. PCT/US2011/037457, filed May 20, 2011, by Vertex Pharmaceuticals Incorporated: International Search Report and Written Opinion, dated Jul. 13, 2011.
International Patent Application No. PCT/US2011/049467, filed Aug. 26, 2011, by Vertex Pharmaceuticals Incorporated: International Search Report and Written Opinion, dated Apr. 2, 2012.

(56) References Cited

OTHER PUBLICATIONS

International Patent Application No. PCT/US2012/034578, filed Apr. 20, 2012, by Vertex Pharmaceuticals Incorporated: International Search Report and Written Opinion, dated Mar. 21, 2013.
International Patent Application No. PCT/US2012/063398, filed Nov. 2, 2012, by Vertex Pharmaceuticals Incorporated: International Search Report and Written Opinion, dated Jan. 23, 2013.
International Patent Application No. PCT/US2013/028097, filed Feb. 27, 2013, by Vertex Pharmaceuticals Incorporated: International Search Report and Written Opinion, dated May 10, 2013.
International Patent Application No. PCT/US2013/044838, filed Jun. 7, 2013, by Vertex Pharmaceuticals Incorporated: International Search Report and Written Opinion, dated Aug. 5, 2013.
International Patent Application No. PCT/US2015/054565, filed Oct. 7, 2015, by Vertex Pharmaceuticals Incorporated: International Search Report and Written Opinion, dated Jan. 11, 2016.
International Search Report and Written Opinion dated Jan. 11, 2016, in International Patent Application No. PCT/US2015/054577.
Irie, K. et al. (1995) "Synthesis of 6-Substituted Indolactams by Microbial Conversion" *Tetrahedron*, 51(22):6255-6266.
Iskandarani, B. et al. (1993) "Simultaneous Optimization of Capsule and Tablet Formulation Using Response Surface Methodology" *Drug Dev Industrial Pharmacy*, 19(16):2089-2101.
Ito, Y. et al. (1996) "Inhibition of GABAA Receptor Chloride Channel by Quinolones and Norfloxacin-Biphenylacetic Acid Hybrid Compounds" *Neuropharmacology*, 35(9/10):1263-1269.
Jivraj, M. et al. (2000 Feb) "An overview of the different excipients useful for the direct compression of tablets" *PSTT*, 3(2):58-63.
Johannesson, J. et al. (Aug. 2012) "CFTR Regulates Early Pathogenesis of Chronic Obstructive Lung Disease in βENaC-Overexpressing Mice" *PLoS ONE*, 7(8):e44059 (11 pages).
Johnson, H.E. et al. (1963) "Reactions of Indole. IV. The Synthesis of Some Aminoindoles" *J Org Chem*, 28(10):2794-2797.
Jones, A.M. and J.M. Helm (2009) "Emerging Treatments in Cystic Fibrosis" *Drugs*, 69(14):1903-1910.
Kaminsky, D. et al. (1968) "Quinolone Antibacterial Agents. Oxolinic Acid and Related Compounds" *J Med Chem*, 11(1):160-163.
Kapranov, N.I. et al. (2004) "Cystic fibrosis: Recent Progress and Problems" *Medical Genetics*, 3(9):398-412, with English translation.
Kurata, H. et al. (2004) "A novel class of apical sodium-dependent bile acid transporter inhibitors: the amphiphilic 4-oxo-1-phenyl-1,4-dihydroquinoline derivatives" *Bioorg. Med. Chem. Lett.*, 14:1183-1186.
Leusen, F.J.J. (1996) "Ab initio prediction of polymorphs" *J Crystal Growth*, 166:900-903.
Levin, M.H. et al. (2005) "CFTR-Regulated Chloride Transport at the Ocular Surface in Living Mice Measured by Potential Differences" *Invest Ophthal Vis Sci*, 46(4):1428-1434.
Loo, T.W. et al. (2011) "Corrector-mediated rescue of misprocessed CFTR mutants can be reduced by the P-glycoprotein drug pump" *Biochem Pharmacol*, 83(3):345-354.
Ma, T. et al. (2002) "High-affinity Activators of Cystic Fibrosis Transmembrane Conductance Regulator (CFTR) Chloride Conductance Identified by High-Throughput Screening" *J. Biol. Chem.*, 277(40):37235-37241.
Mall, M. et al. (2000) "Effect of genistein on native epithelial tissue from normal individuals and CF patients and on ion channels expressed in *Xenopus oocytes*" *Br J Pharmacol*, 130:1884-1892.
Mandour, A.H. et al. (1999) "Aminolysis and Hydrolysis of Indolyl Oxazolones" *Egyptian J Chem*, 42(3):251-266.
Marivingt-Mounir, C. et al. (Feb. 2004) "Synthesis, SAR, crystal structure, and biological evaluation of benzoquinoliziniums as activators of wild-type and mutant cystic fibrosis transmembrane conductance regulator channels" *J Med Chem*, 47(4):962-972.
Martínez-Ohárriz, M.C. (1994) "Polymorphism of diflunisal: Isolation and solid-state characteristics of a new crystal form" *J Pharm Sci*, 83:174-177.
Mashkovskiy, M.D., *Medicaments. Manual for Doctors*. vol. 1, 14th Edition. Moscow: LLC "Novaya Volna", 2001; p. 11.

Miles, E.W. and R.S. Phillips (1985) "Photoinactivation and photoaffinity labeling of tryptophan synthase $\alpha_2\beta_2$ complex by the product analogue 6-azido-L-tryptophan" *Biochem*, 24(17):4694-4703.
Motherwell, W.D.S. et al. (2000) "Automated assignment of graph-set descriptors for crystallographically symmetric molecules" *Acta Cryst*, B56:466-473.
Nishikawa, Y. et al. (1989) "Synthesis and Antiallergic Activity of N-[4-(4-Diphenylmethyl-1-piperazinyl)butyl]-1,4-dihydro-4-oxopyridine-3-carboxamides" *Chem Pharm Bull*, 37(5):1256-1259.
Noone, P.G. et al. (2001) "'CFTR-opathies': disease phenotypes associated with cystic fibrosis transmembrane regulator gene mutations" *Respiratory Research*, 2(6):328-332.
Nosova, E.V., et al. (2002) "Synthesis of new fluorinated derivatives of Quinolinecarboxylic acids" *Chem. of Heter. Compounds*, 38(8):922-928. Translated from: *Khimiya Geterotsiklicheskikh Soedinenii*, No. 8, pp. 1060-1066.
Notice of Allowability for U.S. Appl. No. 14/579,098, dated Apr. 18, 2016.
Notice of Allowance and Fee(s) Due for U.S. Appl. No. 13/290,491, dated Oct. 25, 2012.
Notice of Allowance and Fee(s) Due for U.S. Appl. No. 13/871,349, dated Apr. 17, 2015.
Notice of Allowance and Fee(s) Due for U.S. Appl. No. 13/871,349, dated Aug. 12, 2014.
Notice of Allowance and Fee(s) Due for U.S. Appl. No. 13/871,349, dated Oct. 13, 2015.
Notice of Allowance and Fee(s) Due for U.S. Appl. No. 13/887,839, dated Feb. 2, 2015.
Notice of Allowance and Fee(s) Due for U.S. Appl. No. 13/887,839, dated Jul. 7, 2014.
Notice of Allowance and Fee(s) Due for U.S. Appl. No. 13/887,839, dated Oct. 16, 2014.
Notice of Allowance and Fee(s) Due for U.S. Appl. No. 13/887,839, dated Sep. 30, 2015.
Notice of Allowance and Fee(s) Due for U.S. Appl. No. 14/027,791, dated Jul. 31, 2015.
Notice of Allowance and Fee(s) Due for U.S. Appl. No. 14/031,360, dated Aug. 14, 2014.
Notice of Allowance and Fee(s) Due for U.S. Appl. No. 14/298,245, dated Jul. 21, 2015.
Notice of Allowance and Fee(s) Due for U.S. Appl. No. 14/298,245, dated Nov. 12, 2015.
Notice of Allowance and Fee(s) Due for U.S. Appl. No. 14/326,930, dated Aug. 14, 2015.
Notice of Allowance and Fee(s) Due for U.S. Appl. No. 14/326,930, dated Dec. 8, 2015.
Notice of Allowance and Fee(s) Due for U.S. Appl. No. 14/334,902, dated Feb. 18, 2016.
Notice of Allowance and Fee(s) Due for U.S. Appl. No. 14/334,902, dated Oct. 19, 2015.
Notice of Allowance and Fee(s) Due for U.S. Appl. No. 14/532,791, dated Jul. 24, 2015.
Notice of Allowance and Fee(s) Due for U.S. Appl. No. 14/532,791, dated Mar. 1, 2016.
Notice of Allowance and Fee(s) Due for U.S. Appl. No. 14/532,791, dated Nov. 6, 2015.
Notice of Allowance and Fee(s) Due for U.S. Appl. No. 14/567,475, dated Jan. 5, 2016.
Notice of Allowance and Fee(s) Due for U.S. Appl. No. 14/567,475, dated Sep. 21, 2015.
Notice of Allowance and Fee(s) Due for U.S. Appl. No. 14/579,098, dated Feb. 1, 2016.
Notice of Allowance and Fee(s) Due for U.S. Appl. No. 14/579,098, dated May 12, 2016.
Notice of Allowance and Fee(s) Due for U.S. Appl. No. 14/656,043, dated Aug. 4, 2016.
Notice of Allowance and Fee(s) Due for U.S. Appl. No. 14/687,286, dated Feb. 10, 2016.
Notice of Allowance and Fee(s) Due for U.S. Appl. No. 14/687,286, dated May 19, 2016.
Notice of Allowance and Fee(s) Due for U.S. Appl. No. 14/687,286, dated Sep. 28, 2016.

(56) References Cited

OTHER PUBLICATIONS

Notice of Allowance and Fee(s) Due for U.S. Appl. No. 14/687,286, dated Dec. 1, 2017.
Notice of Allowance and Fee(s) Due for U.S. Appl. No. 14/687,286, dated May 9, 2018.
Notice of Allowance and Fee(s) Due for U.S. Appl. No. 14/925,804, dated May 17, 2016.
Notice of Allowance and Fee(s) Due for U.S. Appl. No. 15/001,036, dated Feb. 10, 2017.
Notice of Allowance and Fee(s) Due for U.S. Appl. No. 15/001,036, dated May 1, 2018.
Notice of Allowance and Fee(s) Due for U.S. Appl. No. 15/342,999, dated Apr. 17, 2018.
Notice of Allowance and Fee(s) Due for U.S. Appl. No. 15/078,800, dated Mar. 16, 2018.
Paranjape, S.M. et al. (2008) "Atypical Cystic fibrosis and CFTR-Related Diseases" *Clinic Rev Allerg Immunol*, 35(3):116-123.
Paritala, H. et al. (2009) "Benzo(h)quinoline derivatives as G-quadruplex binding agents" *Bioorg Med Chem Lett*, 19(8):1584-1587.
Patel, H. et al. (Aug. 2011) "New pharmaceutical excipients in solid dosage forms—A review" *Intl J Pharm & Life Sci*, 2(8):1006-1019.
Pedemonte, N. et al. (2005) "Phenylglycine and sulfonamide correctors of defective ΔF508 and G551D cystic fibrosis transmembrane conductance regulator chloride-channel gating" *Molecular Pharmacology*, 67(5):1797-1807.
Pedemonte, N. et al. (2005) "Small-molecule correctors of defective ΔF508-CFTR cellular processing identified by high-throughput screening" *J Clin Invest*, 115(9):2564-2571.
Pencharz, P.D. and P.R. Durie (2000) "Pathogenesis of malnutrition in cystic fibrosis, and its treatment" *Clin Nutr*, 19(6):387-394.
Pérez-Guille, B. et al. (2004) "Pharmacokinetics of a cephalone (CQ-M-EPCA) in rats after oral, intraduodenal and intravenous administration" *Intl J Pharm*, 282(1-2):87-94.
Porst, H. and L. Kny (1985) "Zur Struktur der Abbauprodukte von Neostigminbromid (On the Structure of Degradation Products of Neostigmine bromide" *Pharmazie*, 40(5):325-328. German with English translation.
Pubchem Compound No. CID 29877; Database Record No. 19962-04-0; Create Date Jul. 19, 2005 [online]. Retrieved from: http://pubchem.ncbi.nlm.nih.gov/summary/summary.cgi?cid=29877; on Jan. 16, 2014 (4 pages).
Roberts, R.M. (1949) "The reaction of diarylformamidines with ethyl malonate" *J Org Chem*, 14(2):277-284.
Sashida, H. et al. (1990) "Studies of Seven Membered Heterocycles. XXXII. Synthesis of N-Unsubstituted 1H-1, 4-Benzodiazepines Stabilized by Intramolecular Hydrogen Bonding" *Chem Pharm Bull*, 38(11):2919-2925.
Sen, A.B. et al. (1947) "Synthesis of Substituted Dinitrophenyl Ketones, and Phenylacetic Acids. Part I." *J. Indian Chem. Soc.*, 24:268-270.
Sen, A.B., et al. (1948) "Synthesis of Substituted Dinitro Phenylketones and Phenylacetic Acids. Part III." *J Indian Chem Soc*, 25:282-284.
Sen, A.B., et al. (1948) "Synthesis of Substituted Dinitrophenyl Ketones and Phenylacetic Acids. Part IV." *J Indian Chem Soc*, 25(8):403-404.
Settimj, G. et al. (1988) "β-Carbolines as agonistic or antagonistic benzodiazepine receptor ligands. 1. Synthesis of some 5-, 6- and 7-amino derivatives of 3-methoxycarbonyl-β-carboline (β-CCM) and of 3-ethoxycarbonyl-β-carboline (β-CCE)" *J Heterocyclic Chem*, 25(5):1391-1397.
Shead et al. (2007) "Cystic fibrosis transmembrane conductance regulator (CFTR) is expressed in human bone" *Thorax*, 62:650-651.
Shioji, Y. (Jan. 27, 2003) *Manufacture Technology of Solid Preparation*. CMC Publishing Co., Ltd.; pp. 9, 12, and 13 (Japanese).
Showalter, H.D.H. et al. (1996) "Concise Syntheses of the Novel 1H-Pyrrolo[3,2-g]quinazoline Ring System and its [2,3-f] Angular Isomer" *J Org Chem*, 61(3):1155-1158.
Silverman, R.B. (1992) *The Organic Chemistry of Drug Design and Drug Action*. San Diego, CA: Academic Press; pp. 5-51.

Sloane, P.A. et al. (2010) "Translational readthrough of premature stop codons combined with CFTR potentiation: potential for combination CFTR therapy" *Pediatric Pulmonology*, 45(33):313, Abstract 264.
Sloane, P.A. et al. (2012) "A Pharmacologic Approach to Acquired Cystic Fibrosis Transmembrane Conductance Regulator Dysfunction in Smoking Related Lung Disease" *PLoS ONE*, 7(6):e39809 (13 pages).
Srivastava, S.K. et al. (2000) "Quinolones: Novel Probes in Antifilarial Chemotheraphy" *J Med Chem*, 43(11):2275-2279.
Swanepoel, E. et al. (2003) "Quality evaluation of generic drugs by dissolution test: changing the USP dissolution medium to distinguish between active and non-active mebendazole polymorphs" *Eur J Pharma Biopharma*, 55:345-349.
Tao, T. (Dec. 31, 2011) "The progress and applications of flavoring and taste-masking technologies in new oral dosage forms" *Shanghai Medical & Pharmaceutical Journal*, 32(5):252-255 (Chinese; English Abstract on p. 252).
Thomson Scientific, Database WPI, Accession No. 2001-425173; Week 200145.
Thomson, S.A. et al. (2009) "Minitablets: New Modality to Deliver Medicines to Preschool-Aged Children" *Pediatrics*, 123:e235 (6 pages).
Tissen, C. et al. (2011) "Development of mini-tablets with 1 mm and 2 mm diameter" *Int J Pharmaceutics*, 416:164-170.
Tonghui, M.A. et al. (2002) "High-affinity Activators of Cystic Fibrosis Transmembrane Conductance Regulator (CFTR) Chloride Conductance Identified by High-throughput Screening" *J Biol Chem*, 277(40):37235-37241.
Tsui, L-C. (1992) "Mutations and Sequence Variations Detected in the Cystic Fibrosis Transmembrane Conductance Regulator (CFTR) Gene: A Report From the Cystic Fibrosis Genetic Analysis Consortium" *Human Mutation*, 1:197-203.
Tzetis, M. et al. (2001) "CFTR gene mutations—including three novel nucleotide substitutions—and haplotype background in patients with asthma, disseminated bronchiectasis and chronic obstructive pulmonary disease" *Hum Genet*, 108:216-221.
U.S. Department of Health and Human Services, Food and Drug Administration (Dec. 2002) *Guidance for Industry. Food-Effect Bioavailability and Fed Bioequivalence Studies*. (9 pages).
U.S. Appl. No. 15/643,182, filed Jul. 6, 2017, by Frederick F. Van Goor, et al.
U.S. Appl. No. 15/898,683, filed Feb. 19, 2018, by Frederick F. Van Goor, et al.
U.S. Appl. No. 15/937,564, filed Mar. 27, 2018, by Frederick F. Van Goor, et al.
U.S. Appl. No. 15/949,404, filed Apr. 10, 2018, by Sara Sabina Hadida Ruah.
Van Es, T. et al. (2001) "N,1-Dialkyl-7-(alkylamino)-4-(alkylimino)-1,4-dihydroquinoline-3-carboxamides and their 4-oxo derivatives: Synthesis and properties" *S. Afr. J. Chem.*, 54:102-117.
Van Es, T. et al. (2002) "1-alkyl-1,4-dihydro-4-iminoquinoline-3-carboxylic acids: Synthesis, Structure, and Properties" *S. Afr. J. Chem.*, 55:13-33.
Van Goor, F. et al. (2006) "Rescue of ΔF580-CFTR trafficking and gating in human cystic fibrosis airway primary cultures by small molecules" *Am J Physiol Lung Cell Mol Physiol*, 290(6):L1117-L1130.
Van Goor, F. et al. (2009) "Rescue of Cf airway epithelial cell function in vitro by a CFTR potentiator, VX-770" *J. Cystic Fibrosis*, vol. 8, Supplement 2, Abstracts of the 32nd European Cystic Fibrosis Conference Jun. 10-13, 2009, Abstract 67, p. S17.
Van Goor, F. et al. (2009) "Rescue of CF airway epithelial cell function in vitro by a CFTR potentiator, VX-770" *PNAS*, 106(44):18825-18830.
Vertex Pharmaceuticals, Inc. (May 17, 2006) "Vertex Pharmaceuticals Initiates Phase I Development for VX-770 in Cystic Fibrosis" [online]. Retrieved from: http://files.shareholder.com/downloads/VRTX/641260063x0x84745/fc8ddd6d-3713-48bb-b689-0444fc7ad623/VRTX_News_2006_5_17_General.pdf (2 pages).
Vertex Pharmaceuticals, Inc. (Aug. 5, 2009) "Study of VX-770 in Cystic Fibrosis Subjects Age 12 and Older Homozygous for the F508del-CFTR Mutation" [online]. ClinicalTrials.gov, Identifier:

(56) References Cited

OTHER PUBLICATIONS

NCT00953706. Retrieved from the Internet: http://clinicaltrials.gov/archive/NCT00953706/2009_08_05, on Jul. 10, 2013 (2 pages).
Vertex Pharmaceuticals, Inc. (Jul. 12, 2010) "Study of the Effect of VX-770 on Hyperpolarized Helium-3 Magnetic Resonance Imaging in Subjects With Cystic Fibrosis and the G551D Mutation" [online]. *ClinicalTrials.gov*, Identifier: NCT01161537. Retrieved from the Internet: http://clinicaltrials.gov/archive/NCT01262352/2010_12_16, on Jul. 9, 2013 (2 pages).
Vertex Pharmaceuticals, Inc. (Oct. 31, 2011) "Study of VX-809 Alone and in Combination With VX-770 in Cystic Fibrosis (CF) Patients Homozygous or Heterozygous for the F508del-CFTR Mutation" [online]. *ClinicalTrials.gov*, Identifier: NCT01225211. Retrieved from the Internet: http://clinicaltrials.gov/archive/NCT01225211/2011_10_31, on Jul. 10, 2013 (2 pages).
Vertex Pharmaceuticals, Inc. (Jan. 2012) *KALYDECO™ (ivacaftor) Tablets. Patient Information.* Reference ID: 3079771 (13 pages).
Vestner, A. et al. (2008) "Neue Therapieansatze bei Cystischer Fibrose (New Therapy Approaches in Cystic Fibrosis)" *Pharmazie in unserer Zeit*, 37(5):354-355. doi:10.1002/pauz.200890069, with English translation.
Wentland, M.P. et al. (1993) "Mammalian Topoisomerase II Inhibitory Activity of 1-Cyclopropyl-6,8-difluoro-1,4-dihydro-7-(2,6-dimethyl-4-pyridinyl)-4-oxo-3-guinolinecarboxylic Acid and Related Derivatives" *J Med Chem*, 36:2801-2809.
Wu, L-S. et al. (1994) "Investigation of moricizine hydrochloride polymorphs" *J Pharm Sci*, 83(10):1404-1406.
Xu, W. et al. (Dec. 31, 2005) "Drug administration and dosage forms for children" *Journal of Pharmaceutical Practice*, 23(2):119-120 (Chinese).
Yu, H. et al. (2010) "VX-770, an investigational CFTR potentiator, acts on multiple CFTR forms in vitro" *Pediatric Pulmonology*, 45(33):318-319, Abstract 280.
Yu, H. et al. (2012) "Ivacaftor potentiation of multiple CFTR channels with gating mutations" *J Cystic Fibrosis*, 11(3):237-245.
Zeitlin, P.L. (2000) "Pharmacologic restoration of ΔF508 CFTR-mediated chloride current" *Kidney International*, 57:832-837.
Zubrick, J.W. (1988) *The Organic Chem Lab Survival Manual. A Student's Guide to Techniques.* New York: John Wiley & Sons, Inc.; 346 pages.
Alhalaweh, A. et al. (2015) "Physical stability of drugs after storage above and below the glass transition temperature: Relationship to glass-forming ability" *Int J Pharm*, 495(1):312-317.
Aulton, M.E. (Ed.) (2007) *Pharmaceutics: The Science of Dosage Design.* 3rd Ed. Churchill Livingston; p. 340.
Aungst, B.J. et al. (1987) "Prodrugs for improved oral nalbuphine bioavailability: inter-species differences in the disposition of nalbuphine and its acetylsalicylate and anthranilate esters" *Int. J. Pharm.*, 38:199-209.
Baghel, S. et al. (2016) "Polymeric Amorphous Solid Dispersions: A Review of Amorphization, Crystallization, Stabilization, Solid-State Characterization, and Aqueous Solubilization of Biopharmaceutical Classification System Class II Drugs" *J Pharm Sci*, 105(9):2527-2544.
Bauer, K.H. et al. (2007) *Lehrbuch der Pharmazeutischen Technologie.* Stuttgart: Wissenschaftliche Verlagsgesellschaft mbH; pp. 214-217, with English translation.
Clemence, F. et al. (Jul. 1988) "4-Hydroxy-3-quinolinecarboxamides with antiarthritic and analgesic activities" *J Med Chem*, 31(7):1453-1462.
Cheung, J. et al. (2008 Febl) "Misfolding of the cystic fibrosis transmembrane conductance regulator and disease" *Biochemistry*, 47(6):1465-1473.
Chiou, W.L. et al. (1971) "Pharmaceutical Applications of Solid Dispersion Systems" J Pharm Sci, 60(9):1281-1302.

Cystic Fibrosis Centre at the Hospital for Sick Children in Toronto, *Cystic Fibrosis Mutation Database.* [online] Retrieved from: http://www.genet.sickkids.on.ca/cftr/app, on Jul. 20, 2018.
Dean, M. et al. (Jun. 1990) "Multiple mutations in highly conserved residues are found in mildly affected cystic fibrosis patients" Cell, 61:863-870.
European Patent Application No. 06848237.1 (Patent No. 1993360), filed Mar. 31, 2008, by Vertex Pharmaceuticals Inc.: Opposition Submission by Georg Kalhammer and Stephan Teipel, Apr. 12, 2019 (6 pages).
European Patent Application No. 06848237.1 (Patent No. 1993360), filed Mar. 31, 2008, by Vertex Pharmaceuticals Inc.: Notice of Opposition by Georg Kalhammer and Stephan Teipel, Nov. 3, 2017 (10 pages).
Gardner, C.R. et al. (2004) "Drugs as Materials: Valuing Physical Form in Drug Discovery" *Nat Rev Drug Discov*, 3:926-934.
Hancock, B. and Zografi, G. (1997) "Characteristics and significance of the amorphous state in pharmaceutical systems" *J Pharm Sci*, 86(1):1-12.
Hegde, S. et al. (2006) "To Market, To Market—2005" *Annu Rep Med Chem*, 41:439-477.
Huang, Y. and Dai, W. G. (2014) "Fundamental aspects of solid dispersion technology for poorly soluble drugs" *Acta Pharm Sin B*, 4(1):18-25.
Jermain, S. V. et al. (2018) "Amorphous solid dispersions and nanocrystal technologies for poorly water-soluble drug delivery—An update" *Int J Pharm*, 535(1-2):379-392.
Mullins, J.D. et al. (1960) "Some Pharmaceutical Properties of Novobiocin" *J. Am. Pharm. Assoc.* 49(4):245-248.
Newman, A. et al. (2012) "Assessing the performance of amorphous solid dispersions" *J Pharm Sci*, 101(4):1355-1377.
Notice of Allowance and Fee(s) Due for U.S. Appl. No. 15/152,092, dated May 17, 2018.
Notice of Opposition for EP Patent Application No. 06848237.1, dated Nov. 15, 2017.
Rahman, Z. et al. (2013) "Tacrolimus Properties and Formulations: Potential Impact of Product Quality on Safety and Efficacy" 1-39.
Serajuddin, A. (1999) "Solid Dispersion of Poorly Water-Soluble Drugs: Early Promises, Subseqeunt Problems, and Recent Breakthroughs" *J. Pharm. Sci.*, 68(10):1058-1066.
Sekiguchi, K. et al. (1961) "Studies on Absorption of Eutectic Mixture. I. A Comparison of the Behavior of Eutectic Mixture of Sulfathazole and that of Ordinary Sulfathiazole in Man" *Chem. Pharm. Bull.* 9:866-872.
Shangari, N. et al. (2005) "Sulfation and Glucuronidation of Phenols: Implications in Coenzyme Q Metabolism" *Methods Enzymol*, 400:342-359.
Stella, V.J. et al. (1999) "Aqueous Solubility and Dissolution Rate Does Not Adequately Predict in vivo Performance: A probe Utilizing Some N-Acyloxymethyl Phenytoin Prodrugs" *J Pharm Sci*, 88(8):775-779.
Summary of Product Characteristics for Telxir® and Agenerase®.
Tanno, F. et al. (2004) "Evaluation of Hypromellose Acetate Succinate (HPMCAS) as a Carrier in Solid Dispersions" *Drug Dev Ind Pharm*, 30(1):9-17.
Thomas, V.H. et al. (2006) "The road map to oral bioavailability: an industrial perspective" *Expert Opin Drug Metabol Toxicol*, 2(4):591-608.
U.S. Appl. No. 16/035,938, filed Jul. 16, 2018, by Rossitza Gueorguieva Alargova et al.
U.S. Appl. No. 16/059,724, filed Aug. 9, 2018, by Tanoury et al.
U.S. Appl. No. 60/754,381, filed Dec. 28, 2005, by Patricia Hurter.
U.S. Appl. No. 16/109,931, filed Aug. 23, 2018, by Keshavarz-Shokri et al.
U.S. Appl. No. 16/276,887, filed Feb. 15, 2019, by Sara S. Hadida Ruah et al.

\* cited by examiner

SOLID FORMS OF N-[2,4-BIS(1,1-DIMETHYLETHYL)-5-HYDROXYPHENYL]-1,4-DIHYDRO-4-OXOQUINOLINE-3-CARBOXAMIDE

CLAIM OF PRIORITY

This application is a continuation of U.S. patent application Ser. No. 15/584,324, filed May 2, 2017, now U.S. Pat. No. 9,931,334; which is a continuation of U.S. patent application Ser. No. 14/852,892, filed Sep. 14, 2015, now U.S. Pat. No. 9,670,163; which is a continuation of U.S. patent application Ser. No. 14/272,692, filed May 8, 2014, now U.S. Pat. No. 9,139,530; which is a continuation of U.S. patent application Ser. No. 13/785,692, filed Mar. 5, 2013, now U.S. Pat. No. 8,754,224; which is a continuation of U.S. patent application Ser. No. 13/358,778, filed Jan. 26, 2012, now U.S. Pat. No. 8,410,274; which is a continuation of U.S. patent application Ser. No. 11/647,505, filed Dec. 28, 2006, now abandoned; which claims priority under 35 USC § 119(e) to U.S. Patent Application Ser. No. 60/754,381, filed on Dec. 28, 2005, the entire contents of which are hereby incorporated by reference.

TECHNICAL FIELD OF THE INVENTION

The present invention relates to solid state forms, for example, crystalline and amorphous forms, of N-[2,4-bis(1,1-dimethylethyl)-5-hydroxyphenyl]-1,4-dihydro-4-oxoquinoline-3-carboxamide, pharmaceutical compositions thereof, and methods therewith.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:10664073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M, et al. (1990) Cell 61:863:870; and Kerem, B-S. et al. (1989) Science 245:1073-1080; Kerem, B-S et al. (1990) Proc. Natl. Acad. Sci, USA 87:844798451). To date, >1000 disease causing mutations in the CF gene have been identified (http://www.genet.sickkids.on.ca/ftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CM. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR, (Dalemans et al. (1991), Nature Loud. 354; 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPE) is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögren's syndrome. Increasing anion secretion via CFTR would enhance fluid transport from the corneal endothelial cells and secretory glands surrounding the eye to increase conical hydration. This would help to alleviate the symptoms associated with dry eye disease. Sjögren's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymyositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. Infect, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, hoagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyctransferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to α1-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders a such as Huntington, spinocerebellar ataxia type I, spinal and bulbar muscular atrophy, dentatorubal pallidoluysian, and myotonic dystrophy, as well as spongiform encephalopathies, such as hereditary Creutzfeldt-Jakob disease (due to priori protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E. coli* (ETEC) having the K99 pilus antigen. Common viral causes of diarrhea include rotavirus and coronavirus. Other infectious agents include *cryptosporidium, giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for stable polymorphic forms of modulators of CFTR activity, such as Compound 1, that can be used to modulate the activity of CFTR in the cell membrane of a mammal.

There is a need for methods of treating CFTR-mediated diseases using such modulators of CFTR activity.

SUMMARY OF THE INVENTION

The present invention relates to solid forms of N-[2,4-bis (1,1-dimethylethyl)-5-hydroxyphenyl]-1,4-dihydro-4-oxo-quinoline-3-carboxamide (hereinafter "Compound 1") which has the structure below:

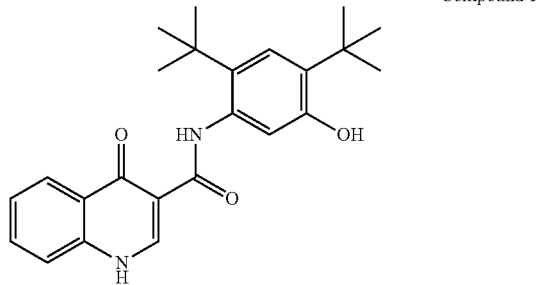

Compound 1

The solid forms of Compound 1 and pharmaceutically acceptable compositions thereof are useful for treating or lessening the severity of a variety of CFTR mediated diseases. Compound 1 is known as both N-[2,4-bis(1,1-dimethylethyl)-5-hydroxyphenyl]-1,4-dihydro-4-oxoquinoline-3-carboxamide and N-(5-hydroxy-2,4-di-tert-butyl-phenyl)-4-oxo-1H-quinoline-3-carboxamide.

In one aspect, the invention features solid amorphous N-[2,4-bis(1,1-dimethylethyl)-5-hydroxyphenyl]-1,4-dihydro-4-oxoquinoline-3-carboxamide. In some embodiments, the solid amorphous N-[2,4-bis(1,1-dimethylethyl)-5-hydroxyphenyl]-1,4-dihydro-4-oxoquinoline-3-carboxamide comprises less than about 15% crystalline N-[2,4-bis(1,1-dimethylethyl)-5-hydroxyphenyl]-1,4-dihydro-4-oxoquinoline-3-carboxamide.

In one aspect, the invention features a preparation of amorphous N-[2,4-bis(1,1-dimethylethyl)-5-hydroxyphenyl]-1,4-dihydro-4-oxoquinoline-3-carboxamide substantially free of crystalline N-[2,4-bis(1,1-dimethylethyl)-5-hydroxyphenyl]-1,4-dihydro-4-oxoquinoline-3-carboxamide.

In some embodiments, the preparation further comprises a surfactant, polymer, or inert pharmaceutically acceptable substance.

In some embodiments, the preparation comprises a solid dispersion, a mixture or a liquid dispersion.

In some embodiments, the preparation comprises solid particles.

In some embodiments, the preparation comprises less than about 15% of crystalline N-[2,4-bis(1,1-dimethylethyl)-5-hydroxyphenyl]-1,4-dihydro-4-oxoquinoline-3-carboxamide.

In some embodiments, the amorphous N-[2,4-bis(1,1-dimethylethyl)-5-hydroxyphenyl]-1,4-dihydro-4-oxoquinoline-3-carboxamide has a particle size distribution of D10, less than 5 μm. In some embodiments, the amorphous N-[2,4-bis(1,1-dimethylethyl)-5-hydroxyphenyl]-1,4-dihydro-4-oxoquinoline-3-carboxamide have a particle size distribution of D50, less than 17 μm. In some embodiments, the amorphous N-[2,4-bis(1,1-dimethylethyl)-5-hydroxyphenyl]-1,4-dihydro-4-oxoquinoline-3-carboxamide have a particle size distribution of D90, less than 100 μm.

In one aspect, the invention features a solid dispersion comprising amorphous N-[2,4-bis(1,1-dimethylethyl)-5-hydroxyphenyl]-1,4-dihydro-4-oxoquinoline-3-carboxamide.

In some embodiments, the solid dispersion comprises less than about 40% of crystalline N-[2,4-bis(1,1-dimethylethyl)-5-hydroxyphenyl]-1,4-dihydro-4-oxoquinoline-3-carboxamide. In some embodiments, the solid dispersion is substantially free of crystalline N-[2,4-bis(1,1-dimethylethyl)-5-hydroxyphenyl]-1,4-dihydro-4-oxoquinoline-3-carboxamide.

In some embodiments, the solid dispersion further comprises a surfactant, polymer, or inert pharmaceutically acceptable substance. For example, the solid dispersion comprises a polymer, and the polymer is one or more than one water-soluble polymer or partially water-soluble polymer.

In some embodiments, the N-[2,4-bis(1,1-dimethylethyl)-5-hydroxyphenyl]-1,4-dihydro-4-oxoquinoline-3-carboxamide has improved physical or chemical stability relative to amorphous N-[2,4-bis(1,1-dimethylethyl)-5-hydroxyphenyl]-1,4-dihydro-4-oxoquinoline-3-carboxamide without being in the presence of polymer.

In some embodiments, the solid dispersion has a higher glass transition temperature than the glass transition temperature of neat amorphous N-[2,4-bis(1,1-dimethylethyl)-5-hydroxyphenyl]-1,4-dihydro-4-oxoquinoline-3-carboxamide.

In some embodiments, the polymer is hydroxypropylmethylcellulose (HPMC). In some embodiments, the polymer is hydroxypropylmethylcellulose acetate succinate (HPMCAS). In some embodiments, the polymer is vinylpyrrolidone/vinyl acetate copolymer (PVP/VA). In some embodiments, the polymer is present in an amount of from about 10% by weight to about 80% by weight, for example, the polymer is present in an amount of less than about 70% by weight, the polymer is present in an amount of about 50% by weight, or the polymer is present in an amount of about 49.5% by weight.

In some embodiments, the N-[2,4-bis(1,1-dimethylethyl)-5-hydroxyphenyl]-1,4-dihydro-4-oxoquinoline-3-carboxamide is present in an amount of from about 10% by weight to about 80% by weight, for example, the N-[2,4-bis(1,1-dimethylethyl)-5-hydroxyphenyl]-1,4-dihydro-4-oxoquinoline-3-carboxamide is present in an amount of less than about 70% by weight or the N-[2,4-bis(1,1-dimethylethyl)-5-hydroxyphenyl]-1,4-dihydro-4-oxoquinoline-3-carboxamide is present in an amount of about 50% by weight.

In some embodiments, the solid dispersion comprises a surfactant, for example, sodium lauryl sulfate. In some embodiments, the surfactant is present in an amount from about 0.1 to about 5%, for example, the surfactant is present in 0.5%.

In some embodiments, at least about 80% by weight of the N N-[2,4-bis(1,1-dimethylethyl)-5-hydroxyphenyl]-1,4-dihydro-4-oxoquinoline-3-carboxamide is in an amorphous form. In some embodiments, substantially all the N-[2,4-bis (1,1-dimethylethyl)-5-hydroxyphenyl]-1,4-dihydro-4-oxo-quinoline-3-carboxamide is in an amorphous form.

In some embodiments, the solid dispersion is obtained by spray drying.

In one aspect, the invention features a pharmaceutical composition comprising amorphous N-[2,4-bis(1,1-dimethylethyl)-5-hydroxyphenyl]-1,4-dihydro-4-oxoquinoline-3-carboxamide. In some embodiments, the amorphous N-[2,4-bis(1,1-dimethylethyl)-5-hydroxyphenyl]-1,4-dihydro-4-oxoquinoline-3-carboxamide is substantially free of crystalline N-[2,4-bis(1,1-dimethylethyl)-5-hydroxyphenyl]-1,4-dihydro-4-oxoquinoline-3-carboxamide.

In one aspect, the invention features, a pharmaceutical composition comprising an amorphous N-[2,4-bis(1,1-dimethylethyl)-5-hydroxyphenyl]-1,4-dihydro-4-oxoquinoline-3-carboxamide as a solid dispersion and one or more of a surfactant, polymer, inert pharmaceutically acceptable substance, or pharmaceutically acceptable carrier.

In some embodiments, the solid dispersion comprises a polymer and wherein the polymer is one or more than one water-soluble polymer or partially water-soluble polymer.

In some embodiments, the solid dispersion has a higher glass transition temperature than the glass transition temperature of neat amorphous N-[2,4-bis(1,1-dimethylethyl)-5-hydroxyphenyl]-1,4-dihydro-4-oxoquinoline-3-carboxamide.

In some embodiments, the polymer is HPMC. In some embodiments, the polymer is HPMCAS. In some embodiments, the polymer is PVP/VA.

In one aspect, the invention features a pharmaceutical composition comprising:

an amorphous solid dispersion of N-[2,4-bis(1,1-dimethylethyl)-5-hydroxyphenyl]-1,4-dihydro-4-oxoquinoline-3-carboxamide wherein said N-[2,4-bis(1,1-dimethylethyl)-5-hydroxyphenyl]-1,4-dihydro-4-oxoquinoline-3-carboxamide comprises about 30-75% wt/wt of the pharmaceutical composition, one or more polymer selected from the group of HPMC and HPMCAS, wherein said polymer is comprises about 30-75% wt/wt of the pharmaceutical composition, and a surfactant, wherein said surfactant comprises about 0.25-1% wt/wt of the pharmaceutical composition.

In some embodiments, the polymer is HPMCAS. In some embodiments, the polymer is HPMC.

In some embodiments, the surfactant is sodium laurel sulfate.

In some embodiments, said N-[2,4-bis(1,1-dimethylethyl)-5-hydroxyphenyl]-1,4-dihydro-4-oxoquinoline-3-carboxamide comprises about 50% wt/wt of the pharmaceutical composition, said polymer is HPMCAS and comprises about 49.5% wt/wt of the pharmaceutical composition, and a said surfactant is sodium laurel sulfate and comprises about 0.5% wt/wt of the pharmaceutical composition.

In one aspect, the invention features a pharmaceutical composition comprising;

an aqueous suspension comprising amorphous N-[2,4-bis(1,1-dimethylethyl)-5-hydroxyphenyl]-1,4-dihydro-4-oxoquinoline-3-carboxamide particles and a pharmaceutically acceptable carrier.

In some embodiments, the pharmaceutically acceptable carrier is a polymer in solution selected from the group of HPMC and HPMCAS. In some embodiments, the pharmaceutically acceptable carrier is a polymer in solution is PVP/VA.

In some embodiments, the amorphous compound is in the form of a solid dispersion.

In some embodiments, the pharmaceutical composition further comprises a surfactant, either in the solution or as a component of the solid dispersion, for example, SLS. In some embodiments, the polymer is either in the solution or as a component of the solid dispersion particles or both. In some embodiments, the aqueous suspension comprises from about 01% to about 20% by weight of the surfactant. In some embodiments, the aqueous suspension comprises from about 0.1% to about 2.0% by weight of polymer, for example, about 1% by weight of polymer.

In one aspect, the invention features a process for preparing an amorphous form of N-[2,4-bis(1,1-dimethylethyl)-5-hydroxyphenyl]-1,4-dihydro-4-oxoquinoline-3-carboxamide comprising spray-drying N-[2,4-bis(1,1-dimethylethyl)-5-hydroxyphenyl]1,4-dihydro-4-oxoquinoline-3-carboxamide to provide an amorphous form of N-[2,4-bis(1,1-dimethylethyl)-5-hydroxyphenyl]-1,4-dihydro-4-oxoquinoline-3-carboxamide.

In some embodiments, the method comprises combining N-[2,4-bis(1,1-dimethylethyl)-5-hydroxyphenyl]-1,4-dihydro-4-oxoquinoline-3-carboxamide and a suitable solvent to form a mixture and then spray-drying the mixture to obtain the amorphous form of N-[2,4-bis(1,1-dimethylethyl)-5-hydroxyphenyl]-1,4-dihydro-4-oxoquinoline-3-carboxamide.

In some embodiments, the mixture is a solution N-[2,4-bis(1,1-dimethylethyl)-5-hydroxyphenyl]-1,4-dihydro-4-oxoquinoline-3-carboxamide and the suitable solvent. In some embodiments, the suitable solvent comprises acetone or MEK. In some embodiments, the suitable solvent comprises a mixture of solvents, for example, a mixture of acetone and water or a mixture of MEK and water. In some embodiments, the water in the solvent mixture is present at about 10% wt.

In some embodiments, the method comprises a) forming a mixture comprising N-[2,4-bis(1,1-dimethylethyl)-5-hydroxyphenyl]-1,4-dihydro-4-oxoquinoline-3-carboxamide, a polymer, and a solvent; and b) spray-drying the mixture to form a solid dispersion comprising N-[2,4-bis(1,1-dimethylethyl)-5-hydroxyphenyl]-1,4-dihydro-4-oxoquinoline-3-carboxamide.

In some embodiments, the mixture comprises a solution of N-[2,4-bis(1,1-dimethylethyl)-5-hydroxyphenyl]-1,4-dihydro-4-oxoquinoline-3-carboxamide, the polymer, and the solvent. In some embodiments, the polymer is selected from HPMC and HPMCAS. In some embodiments, the polymer is PVP/VA. In some embodiments, the polymer is present in an amount of from about 30% to about 70% by weight in the solid dispersion. In some embodiments, the mixture further comprises a surfactant, for example, SLS.

In some embodiments, the solvent comprises acetone, for example, a mixture of acetone and water. In some embodiments, the solvent comprises from about 0% to about 20% water and from about 70% to about 100% acetone.

In one aspect, the invention features a solid dispersion prepared according a process described herein.

In one aspect, the invention features a method for treating a CFTR-mediated disease in a mammal comprising administering amorphous N-[2,4-bis(1,1-dimethylethyl)-5-hydroxyphenyl]-1,4-dihydro-4-oxoquinoline-3-carboxamide. In some embodiments, the method comprises administering an amorphous solid dispersion of N-[2,4-bis(1,1-dimethylethyl)-5-hydroxyphenyl]-1,4-dihydro-4-oxoquinoline-3-carboxamide. In some embodiments, the method comprises administering an additional therapeutic agent.

In one aspect, the invention features a pharmaceutical pack or kit comprising amorphous N-[2,4-bis(1,1-dimethylethyl)-5-hydroxyphenyl]-1,4-dihydro-4-oxoquinoline-3-carboxamide and a pharmaceutically acceptable carrier.

In one aspect, the invention features a crystal form of N-[2,4-bis(1,1-dimethylethyl)-5-hydroxyphenyl]-1,4-dihydro-4-oxoquinoline-3-carboxamide, characterized by one or more peaks at from about 4.8 to about 5.2 degrees, for example, about 5.0 degrees, and from about 15.4 to about 15.8 degrees, for example, about 15.6 degrees in an X-ray powder diffraction pattern obtained using Cu K alpha radiation. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 7.6 to about 8.0, e.g., 7.8. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 8.3 to about 8.7, for example, about 8.5. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 9.0 to about 9.4, for example, about 9.2. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 9.7 to about 10.1, for example about 9.9. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 11.7 to about 12.1, for example, about 11.9. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 12.4 to about 12.8, for example, about 12.6. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 13.7 to about 14.1, for example about 13.9. In some embodiments, the crystal form of N-[2,4-bis(1,1-dimethylethyl)-5-hydroxyphenyl]-1,4-dihydro-4-oxoquinoline-3-carboxamide is further characterized by the following peak at from about 14.7 to about 15.1, for example, about 14.9. In some embodiments, the crystal form of N-[2,4-bis(1,1-dimethylethyl)-5-hydroxyphenyl]-1,4-dihydro-4-oxoquinoline-3-carboxamide is further characterized by the following peak from about 16.3 to about 16.7, for example about 16.5. In some embodiments, the crystal form of N-[2,4-bis(1,1-dimethylethyl)-5-hydroxyphenyl]-1,4-dihydro-4-oxoquinoline-3-carboxamide is further characterized by the following peak from about 17.9 to about 18.3, for example, about 18.1. In some embodiments, the crystal form of N-[2,4-bis(1,1-dimethylethyl)-5-hydroxyphenyl]-1,4-dihydro-4-oxoquinoline-3-carboxamide is further characterized by the following peak from about 18.3 to about 18.7, for example, about 18.5. In some embodiments, the crystal form of N-[2,4-bis(1,1-dimethylethyl)-5-hydroxyphenyl]-1,4-dihydro-4-oxoquinoline-3-carboxamide is further characterized by the following peak from about 20.5 to about 20.9, for example, about 20.7. In some embodiments, the crystal form of N-[2,4-bis(1,1-dimethylethyl)-5-hydroxyphenyl]-1,4-dihydro-4-oxoquinoline-3-carboxamide is further characterized by the following peak from about 21.8 to about 22.2, for example, about 22.0. In some embodiments, the crystal form of N-[2,4-bis(1,1-dimethylethyl)-5-hydroxyphenyl]-1,4-dihydro-4-oxoquinoline-3-carboxamide is further characterized by the following peak from about 23.1 to about 23.7, for example, about 23.5. In some embodiments, the crystal form of N-[2,4-bis(1,1-dimethylethyl)-5-hydroxyphenyl]-1,4-dihydro-4-oxoquinoline-3-carboxamide is further characterized by the following peak from about 25.1 to about 25.5, for example, about 25.3. In some embodiments, the crystal form of N-[2,4-bis(1,1-dimethylethyl)-5-hydroxyphenyl]-1,4-dihydro-4-oxoquinoline-3-carboxamide is further characterized by the following peak from about 27.8 to about 28.2, for example, about 28.0. In some embodiments, the crystal form of N-[2,4-bis(1,1-dimethylethyl)-5-hydroxyphenyl]-1,4-dihydro-4-oxoquinoline-3-carboxamide is further characterized by the following peak from about 29.2 to about 29.6, for example, about 29.4. In some embodiments, the crystal form of N-[2,4-bis(1,1-dimethylethyl)-5-hydroxyphenyl]-1,4-dihydro-4-oxoquinoline-3-carboxamide is further characterized by the following peak from about 30.7 to about 31.1, for example, about 30.9. In some embodiments, the crystal form of N-[2,4-bis(1,1-dimethylethyl)-5-hydroxyphenyl]-1,4-dihydro-4-oxoquinoline-3-carboxamide is characterized by an X-ray powder diffraction pattern obtained using Cu K alpha radiation substantially similar to FIG. 4.

In one aspect, the invention features a pharmaceutical composition comprising the crystal form of N-[2,4-bis(1,1-dimethylethyl)-5-hydroxyphenyl]-1,4-dihydro-4-oxoquinoline-3-carboxamide having the characteristics of Form A, for example as described above, and a pharmaceutically acceptable adjuvant or carrier.

In one aspect, the invention features a process for preparing a crystal form of N-[2,4-bis(1,1-dimethylethyl)-5-hydroxyphenyl]-1,4-dihydro-4-oxoquinoline-3-carboxamide of Form A, for example as characterized above, wherein said process comprises the step of heating N N-[2,4-bis(1,1-dimethylethyl)-5-hydroxyphenyl]-1,4-dihydro-4-oxoquinoline-3-carboxamide to about 250° C. and cooling to room temperature.

In one aspect, the invention features a method for treating a CFTR mediated disease in a mammal comprising administering N-[2,4-bis(1,1-dimethylethyl)-5-hydroxyphenyl]-1,4-dihydro-4-oxoquinoline-3-carboxamide of Form A, for example as characterized above. In some embodiments, the N-[2,4-bis(1,1-dimethylethyl)-5-hydroxyphenyl]-1,4-dihydro-4-oxoquinoline-3-carboxamide is a component of a pharmaceutical composition. In some embodiments, the method comprises administering an additional therapeutic agent.

In one aspect, the invention features a pharmaceutical pack or kit comprising crystalline N-[2,4-bis(1,1-dimethylethyl)-5-hydroxyphenyl]-1,4-dihydro-4-oxoquinoline-3-carboxamide of Form A, for example as characterized above and a pharmaceutically acceptable carrier.

In one aspect, the invention features a crystal form of N-[2,4-bis(1,1-dimethylethyl)-5-hydroxyphenyl]-1,4-dihydro-4-oxoquinoline-3-carboxamide, characterized by one or more peaks at from about 6.2 to about 6.6, for example, about 6.4, from about 7.5 to about 7.9, for example, about 7.7, from about 12.5 to about 12.9, for example, about 12.7, and from about 17.9 to about 18.3, for example, about 18.1 degrees in an X-ray powder diffraction pattern obtained using Cu K alpha radiation.

In some embodiments, the crystal form of N-[2,4-bis(1,1-dimethylethyl)-5-hydroxyphenyl]-1,4-dihydro-4-oxoquinoline-3-carboxamide is further characterized by the following peak from about 8.2 to about 8.6, for example, about 8.4. In some embodiments, the crystal form of N-[2,4-bis(1,1-dimethylethyl)-5-hydroxyphenyl]-1,4-dihydro-4-oxoquinoline-3-carboxamide is further characterized by the following peak from about 10.8 to about 11.2, for example, about 11.0. In some embodiments, the crystal form of N-[2,4-bis(1,1-dimethylethyl)-5-hydroxyphenyl]-1,4-dihydro-4-oxoquinoline-3-carboxamide is further characterized by the following peak from about 14.6 to about 15.0, for example, about 14.8. In some embodiments, the crystal form of N-[2,4-bis(1,1-dimethylethyl)-5-hydroxyphenyl]-1,4-dihydro-4-oxoquinoline-3-carboxamide is further characterized by the following peak from about 15.9 to about 16.3, for example, about 16.1. In some embodiments, the crystal form of N-[2,4-bis(1,1-dimethylethyl)-5-hydroxyphenyl]-1,4-dihydro-4-oxoquinoline-3-carboxamide is further characterized by the following peak from about 16.9 to about 17.3, for example, about 17.1. In some embodiments, the crystal form of N-[2,4-bis(1,1-dimethylethyl)-5-hydroxyphenyl]-1,4-dihydro-4-oxoquinoline-3-carboxamide is further characterized by the following peak from about 18.4 to about 18.8, for example, about 18.6. In some embodiments, the crystal form of N-[2,4-bis(1,1-dimethylethyl)-5-hydroxyphenyl]-1,4-dihydro-4-oxoquinoline-3-carboxamide is further characterized by the following peak from about 19.2 to about 19.6, for example, about 19.4. In some embodiments, the crystal form of N-[2,4-bis(1,1-dimethylethyl)-5-hydroxyphenyl]-1,4-dihydro-4-oxoquinoline-3-carboxamide is further characterized by the following peak from about 20.9 to about 21.3, for example, about 21.1. In some embodiments, the crystal form of N-[2,4-bis(1,1-dimethylethyl)-5-hydroxyphenyl]-1,4-dihydro-4-oxoquinoline-3-carboxamide is further characterized by the following peak from about 22.4 to about 22.8, for example, about 22.6. In some embodiments, the crystal form of N-[2,4-bis(1,1-dimethylethyl)-5-hydroxyphenyl]-1,4-dihydro-4-oxoquinoline-3-carboxamide is further characterized by the following peak from about 23.2 to about 23.6, for example, about 23.4. In some embodiments, the crystal form of N-[2,4-bis(1,1-dimethylethyl)-5-hydroxyphenyl]-1,4-dihydro-4-oxoquinoline-3-carboxamide is further characterized by the following peak from about 23.7 to about 24.1, for example, about 23.9. In some embodiments, the crystal form of N-[2,4-bis(1,1-dimethylethyl)-5-hydroxyphenyl]-1,4-dihydro-4-oxoquinoline-3-carboxamide is further characterized by the following peak from about 24.7 to about 25.1, for example, about 24.9. In some embodiments, the crystal form of N-[2,4-bis(1,1-dimethylethyl)-5-hydroxyphenyl]-1,4-dihydro-4-oxoquinoline-3-carboxamide is further characterized by the following peak from about 25.3 to about 25.7, for example, about 25.5. In some embodiments, the crystal form of N-[2,4-bis(1,1-dimethylethyl)-5-hydroxyphenyl]-1,4-dihydro-4-oxoquinoline-3-carboxamide is further characterized by the following peak from about 26.5 to about 26.9, for example, about 26.7. In some embodiments, the crystal form of N-[2,4-bis(1,1-dimethylethyl)-5-hydroxyphenyl]-1,4-dihydro-4-oxoquinoline-3-carboxamide is further characterized by the following peak from about 27.3 to about 27.7, for example, about 27.5. In some embodiments, the crystal form of N-[2,4-bis(1,1-dimethylethyl)-5-hydroxyphenyl]-1,4-dihydro-4-oxoquinoline 3-carboxamide is further characterized by the following peak from about 29.4 to about 29.8, for example, about 29.6. In some embodiments, the crystal form of N-[2,4-bis(1,1-dimethylethyl)-5-hydroxyphenyl]-1,4-dihydro 4-oxoquinoline-3-carboxamide is further characterized by the following peak from about 33.3 to about 33.7, for example, about 33.5. In some embodiments, the crystal form of N-[2,4-bis(1,1-dimethylethyl)-5-hydroxyphenyl]-1,4-dihydro 4-oxoquinoline-3-carboxamide is further characterized by the following peak from about 36.6 to about 37.0, for example, about 36.8. In some embodiments, the crystal form of N-[2,4-bis(1,1-dimethylethyl)-5-hydroxyphenyl]-1,4-dihydro-4-oxoquinoline-3-carboxamide is characterized by an X-ray powder diffraction pattern obtained using Cu K alpha radiation substantially similar to FIG. 7.

In one aspect, the invention features a crystal form of N-[2,4-bis(1,1-dimethylethyl)-5-hydroxyphenyl]-1,4-dihydro-4-oxoquinoline-3-carboxamide, having a monoclinic crystal system, a P21 space grouping, and the following unit cell dimensions:

a=11.8011(7) Å α=90°
b=5.9819(3) Å β=105.110(4)°
c=14.7974(8) Å γ=90°.

In one aspect, the invention features a pharmaceutical composition comprising the crystal form of N-[2,4-bis(1,1-dimethylethyl)-5-hydroxyphenyl]-1,4-dihydro-4-oxoquinoline-3-carboxamide according to Form B, for example, as characterized above, and a pharmaceutically acceptable adjuvant or carrier.

In one aspect, the invention features a process for preparing the crystal form of N-[2,4-bis(1,1-dimethylethyl)-5-hydroxyphenyl]-1,4-dihydro-4-oxoquinoline-3-carboxamide according to Form B, for example, as characterized above, wherein said process comprises the steps of alternatively heating and cooling a slurry of Compound 1 and acetonitrile. In some embodiments, the process comprises heating said slurry at about 50 C for about 12 hours. In some embodiments, said cooling step comprises placing said slurry at room temperature for about 12 hours, followed by cooling at about 0° C. overnight.

In one aspect, the invention features a method of treating a CFTR mediated disease in a patient comprising the step of administering to said patient a crystal form of N-[2,4-bis(1,1-dimethylethyl)-5-hydroxyphenyl]-1,4-dihydro-4-oxoquinoline-3-carboxamide or a pharmaceutical composition comprising a crystal form of N-[2,4-bis(1,1-dimethylethyl)-5-hydroxyphenyl]-1,4-dihydro-4-oxoquinoline-3-carboxamide according to Form B, for example, as characterized above.

In one aspect, the invention features a method of treating a disease is selected from cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders a such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry eye disease, and Sjogren's disease by administering a solid form of Compound 1 as described above, for example, Form A, Form B, or amorphous Compound 1, for example, neat or as a component of a solid dispersion. In some embodiments, the disease is cystic fibrosis.

Processes described herein can be used to prepare the compositions of this invention. The amounts and the features of the components used in the processes would be as described herein.

As used herein, the term "amorphous" refers to a solid material having no long range order in the position of its molecules Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

As used herein, the phrase "substantially amorphous Compound 1" is used interchangeably with the phrase "amorphous Compound 1 substantially free of crystalline Compound 1," In some embodiments, substantially amorphous Compound 1 has less than about 30% crystalline Compound 1, for example, less than about 30% of crystalline Compound 1, e.g., less than about 25% crystalline Compound 1, less than about 20% crystalline Compound 1, less than about 15% crystalline Compound 1, less than about 10% crystalline Compound 1, less than about 5% crystalline Compound 1, less than about 2% crystalline Compound 1. In some preferred embodiments, Compound 1 has less than about 15% crystalline compound 1. Some embodiments include a preparation of substantially amorphous Compound 1, for example having the degree of crystalline Compound 1 as described above.

As used herein "crystalline solids" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

As used herein, a "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase), or alternatively, an amorphous drug (dispersed phase) in an amorphous polymer (continuous phase). In some embodiments an amorphous solid dispersion includes the polymer constituting the dispersed phase, and the drug constitute the continuous phase. In some embodiments, the dispersion includes amorphous Compound 1 or substantially amorphous Compound 1.

The term "solid amorphous dispersion" generally refers to a solid dispersion of two or more components, usually a drug and polymer, but possibly containing other components such as surfactants or other pharmaceutical excipients, where Compound 1 is amorphous or substantially amorphous (e.g., substantially free of crystalline Compound 1), and the physical stability and/or dissolution and/or solubility of the amorphous drug is enhanced by the other components.

A solid dispersion as provided herein is a particularly favorable embodiment of this invention. Solid dispersions typically include a compound dispersed in an appropriate carrier medium, such as a solid state carrier. In one embodiment, a carrier according to this invention comprises a polymer, preferably, a water-soluble polymer or a partially water-soluble polymer. It would be understood that one or more than one water-soluble polymer could be used in a solid dispersion of this invention.

An exemplary solid dispersion is a co-precipitate or a co-melt of N-[2,4-bis(1,1-dimethylethyl)-5-hydroxyphenyl]-1,4-dihydro-4-oxoquinoline-3-carboxamide with at least one polymer. A "Co-precipitate" is a product after dissolving a drug and a polymer in a solvent or solvent mixture followed by the removal of the solvent or solvent mixture. Sometimes the polymer can be suspended in the solvent or solvent mixture. The solvent or solvent mixture includes organic solvents and supercritical fluids. A "co-melt" is a product after heating a drug and a polymer to melt, optionally in the presence of a solvent or solvent mixture, followed by mixing, removal of at least a portion of the solvent if applicable, and cooling to room temperature at a selected rate. In some cases, the solid dispersions are prepared by adding a solution of a drug and a solid polymer followed by mixing and removal of the solvent. To remove the solvent, vacuum drying, spray drying, tray drying, lyophilization, and other drying procedures may be applied. Applying any of these methods using appropriate processing parameters, according to this invention, would provide N-[2,4-bis(1,1-dimethylethyl)-5-hydroxyphenyl]-1,4-dihydro-4-oxoquinoline-3-carboxamide in an amorphous state in the final solid dispersion product.

DETAILED DESCRIPTION OF THE INVENTION

Figure 1:
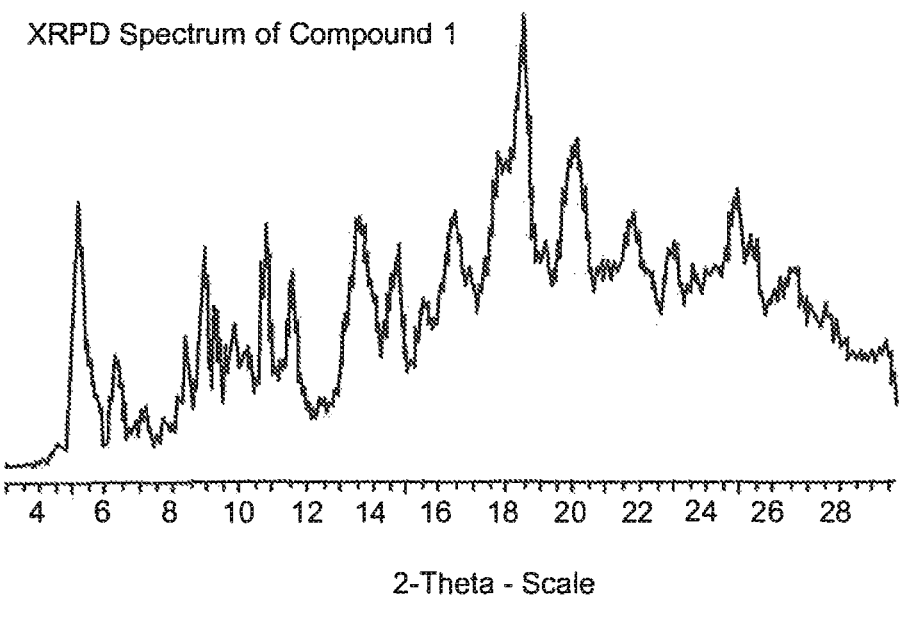
FIG. 1 is an X-Ray powder diffraction pattern of Compound 1.

Solid Forms of Compound 1
Form A
Form A of Compound 1 is characterized by one or more peaks at from about 4.8 to about 5.2, for example, about 5.0, e.g., 4.99, and from about 15.4 to about 15.8, for example, about 15.6 e.g., 15.58 degrees in an X-ray powder diffraction pattern obtained using Cu K alpha radiation (2θ). Other peaks (2θ), which can be characteristic of Form A, include the following: from about 7.6 to about 8.0, for example, about 7.8, e.g., 7.75; from about 8.3 to about 8.7, for example, about 8.5, e.g., 8.46; from about 9.0 to about 9.4, for example, about 9.2, e.g., 9.21; from about 9.7 to about 10.1, for example, about 9.9, e.g., 9.92; from about 11.7 to about 12.1, for example, about 11.9, e.g., 11.93; from about 12.4 to about 12.8, for example, about 12.6, e.g., 12.64; from about 13.7 to about 14.1, for example, about 13.9, e.g., 13.88; from about 14.7 to about 15.1, for example, about 14.9, e.g., 14.91; from about 16.3 to about 16.7, for example, about 16.5, e.g., 16.46; from about 17.9 to about 18.3, for example, about 18.1, e.g., 18.09; from about 18.3 to about 18.7, for example, about 18.5, e.g., 18.52; from about 21.5 to about 21.9, for example, about 21.7, e.g., 20.65; from about 21.8 to about 22.2, for example, about 22.0, e.g., 21.95; from about 23.1 to about 23.7, for example, about 23.5, e.g., 23.49; from about 25.1 to about 25.5, for example, about 25.3, e.g., 25.26; from about 27.8 to about 28.2 for example, about 28.0, e.g., 28.02; from about 29.2 to about 29.6, for example, about 29.4, e.g., 29.35; and about from about 30.7 to about 31.1, for example, 30.9, e.g., 30.85. For example, Form A can be characterized by an X-ray powder diffraction pattern obtained using Cu K alpha radiation substantially similar to FIG. 4.

Pharmaceutical compositions including Form A and a pharmaceutically acceptable adjuvant or carrier, such as a polymer or surfactant are also described. Form A can be formulated in a pharmaceutical composition, in some instances, with another therapeutic agent, for example another therapeutic agent for treating cystic fibrosis or a symptom thereof.

Processes for preparing Form A are exemplified herein.

Methods of treating a CFTR mediated disease, such as cystic fibrosis, in a patient include administering to said patient Form A or a pharmaceutical composition comprising Form A.

Form B

The solid state crystal Form B of Compound 1 is characterized by one or more peaks at from about 6.0 to about 6.4 for example, about 6.2, e.g., 6.17, from about 7.4 to about 7.8 for example, about 7.6, e.g., 7.61, from about 12.1 to about 12.5 for example, about 12.3, e.g., 12.33, and from about 17.8 to about 18.2 for example, about 18.0, e.g., 17.96 degrees in an X-ray powder diffraction pattern obtained using Cu K alpha radiation (2θ). Other peaks (2θ), which can be characteristic of Form B, include the following: from about 8.2 to about 8.6 for example, about 8.4, e.g., 8.40; from about 10.8 to about 11.2 for example, about 11.0, e.g., 11.02; from about 14.6 to about 15.0 for example, about 14.8, e.g., 14.83; from about 15.9 to about 16.3 for example, about 16.1, e.g., 16.14; from about 16.9 to about 17.3 for example, about 17.1, e.g., 17.11; from about 18.4 to about 18.8 for example, about 18.6, e.g., 18.55; from about 19.2 to about 19.6 for example, about 19.4, e.g., 19.43; from about 20.9 to about 21.3 for example, about 21.1, e.g., 21.05; from about 22.4 to about 22.8 for example, about 22.6, e.g., 22.56; from about 23.2 to about 23.6 for example, about 23.4, e.g., 23.37; from about 23.7 to about 24.1 for example, about 23.9, e.g., 23.94; from about 24.7 to about 25.1 for example, about 24.9, e.g., 24.86; from about 25.3 to about 25.7 for example, about 25.5, e.g., 25.50; from about 26.5 to about 26.9 for example, about 26.7, e.g., 26.72; from about 27.3 to about 27.7 for example, about 27.5, e.g., 27.51; from about 29.4 to about 29.8 for example, about 29.6, e.g., 29.60; from about 33.3 to about 33.7 for example, about 33.5, e.g., 33.48; and from about 36.6 to about 37.0 for example, about 36.8, e.g., 36.78. Form B can be further characterized, for example, by an X-ray powder diffraction pattern obtained using Cu K alpha radiation substantially similar to FIG. 7.

Applicants have determined crystal structure dimensions of Form B by analysis of single crystal data. Form B is a monoclinic crystal system having a $P2_1$ space grouping, and the following unit cell dimensions: a @ 11.8011(7) Å, $\alpha=90°$; b=5.9819(3) Å, $\beta=105.110(4)°$ 1; c=14.7974(8) Å, $\gamma=90°$. Additional details about the structure and packing of Form B are provided in the Examples.

Pharmaceutical compositions including Form B and a pharmaceutically acceptable adjuvant or carrier, such as a polymer or surfactant are also described. Form B can be formulated in a pharmaceutical composition, in some instances, with another therapeutic agent, for example another therapeutic agent for treating cystic fibrosis or a symptom thereof.

Processes for preparing Form B are exemplified herein.

Methods of treating a CFTR mediated disease, such as cystic fibrosis, in a patient include administering to said patient Form B or a pharmaceutical composition comprising Form B.

Amorphous Compound 1

Compound 1 can be present as an amorphous solid, for example amorphous Compound 1 as a substantially neat preparation, or amorphous compound 1 as a component as a dispersion such as a solid amorphous dispersion.

In some embodiments, an amorphous form of Compound 1 is substantially free of crystalline Compound 1 (e.g., Form A, Form B or any crystalline form of Compound 1), for example Compound 1 has less than about 30% of crystalline Compound 1, e.g., less than about 25% crystalline Compound 1, less than about 20% crystalline Compound 1, less than about 15% crystalline Compound 1, less than about 10% crystalline Compound 1, less than about 5% crystalline Compound 1, less than about 2% crystalline. Compound 1, preferably less than about 15% crystalline compound 1, Compound 1 can be characterized by an X-ray powder diffraction pattern obtained using Cu K alpha radiation substantially similar to FIG. 11. For example, the substantially amorphous form of Compound 1 can be characterized as having an XRPD having no sharp characteristic crystalline peak(s) in its X-ray power diffraction (XRPD) pattern (i.e., is not crystalline as determined by XRPD). Instead, one or several broad peaks (e.g., halos) appear in its XRPD pattern.

Polymers

Solid dispersions including amorphous Compound 1 and a polymer (or solid state carrier) also are included herein. For example, Compound 1 is present as an amorphous compound as a component of a solid amorphous dispersion. The solid amorphous dispersion, generally includes Compound 1 and a polymer. Exemplary polymers include cellulosic polymers such as HPMC or HPMCAS and pyrrolidone containing polymers such as PVP/VA. In some embodiments, the solid amorphous dispersion includes one or more additional excipients, such as a surfactant.

In one embodiment, a polymer is able to dissolve in aqueous media. The solubility of the polymers may be pH-independent or pH-dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer should be chemically and biologically inert. In order to improve the physical stability of the solid dispersions, the glass transition temperature ($T_g$) of the polymer should be as high as possible. For example, preferred polymers have a glass transition temperature at least equal to or greater than the glass transition temperature of the drug (e.g., Compound 1). Other preferred polymers have a glass transition temperature that is within about 10 to about 15° C. of the drug (e.g., Compound 1). Examples of suitable glass transition temperatures of the polymers include at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., or at least about 175° C. (as measured under dry conditions). Without wishing to be bound by theory, it is believed that the underlying mechanism is that a polymer with a higher $T_g$ generally has lower molecular mobility at room temperature, which can be a crucial factor in stabilizing the physical stability of the amorphous solid dispersion.

Additionally, the hygroscopicity of the polymers should be as low, e.g., less than about 10%. For the purpose of comparison in this application, the hygroscopicity of a polymer or composition is characterized at about 60% relative humidity. In some preferred embodiments, the polymer has less than about 10% water absorption, for example less than about 9%, less than about 8%, less than about 7%, less than about 6%, less than about 5%, less than about 4%, less than about 3%, or less than about 2% water absorption. The hygroscopicity can also affect the physical stability of the solid dispersions. Generally, moisture adsorbed in the polymers can greatly reduce the $T_g$ of the polymers as well as the resulting solid dispersions, which will further reduce the physical stability of the solid dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins β-cyclodextrin) and copolymers and derivatives thereof, including for example PVP-VA (polyvinylpyrrolidone-vinyl acetate).

In some preferred embodiments, the polymer is hydroxypropylmethylcellulose (HPMC), such as HPMC E50, HPMCE15, or HPMC60SH50).

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAD), or polymethacrylates (e.g., Eudragit® S). In some preferred embodiments, the polymer is hydroxypropyl methyl cellulose acetate succinate (HPMCAS).

In yet another embodiment, the polymer is a polyvinylpyrrolidone co-polymer, for example, a vinylpyrrolidone/vinyl acetate co-polymer (PVP/VA).

In embodiments where Compound 1 forms a solid dispersion with a polymer, for example with an HPMC, HPMCAS or PVP/VA polymer, the amount of polymer relative to the total weight of the solid dispersion ranges from about 0.1% to 99% by weight. Unless otherwise specified, percentages of drug, polymer and other excipients as described within a dispersion are given in weight percentages. The amount of polymer is typically at least about 20%, and preferably at least about 30%, for example, at least about 35%, at least about 40%, at least about 45%, or about 50% (e.g., 49.5%). The amount is typically about 99% or less, and preferably about 80% or less, for example about 75% or less, about 70% or less, about 65% or less, about 60% or less, or about 55% or less. In one embodiment, the polymer is in an amount of up to about 50% of the total weight of the dispersion (and even more specifically, between about 40% and 50%, such as about 49%, about 49.5%, or about 50%). HPMC and HPMCAS are available in a variety of grades from ShinEtsu, for example, HPMCAS is available in a number of varieties, including AS-LE, AS-MF, AS-HF, AS-LO, AS-MG, AS-HG. Each of these grades vary with the percent substitution of acetate and succinate.

In some preferred embodiments, Compound 1 and polymer are present in roughly equal amounts, for example each of the polymer and the drug make up about half of the percentage weight of the dispersion. For example, the polymer is present in about 49.5% and the drug is present in about 50%.

In some preferred embodiments, the dispersion further includes other minor ingredients, such as a surfactant (e.g., SLS). In some preferred embodiments, the surfactant is present in less than about 10% of the dispersion, for example less than about 9%, less than about 8%, less than about 7%, less than about 6%, less than about 5%, less than about 4%, less than about 3%, less than about 2%, about 1%, or about 0.5%.

In embodiments including a polymer, the polymer should be present in an amount effective for stabilizing the solid dispersion. Stabilizing includes inhibiting or preventing, the crystallization of Compound 1. Such stabilizing would inhibit the conversion Compound 1 from amorphous to crystalline form. For example, the polymer would prevent at least a portion (e.g., about 5%, about 10%, about 15%, about 20%, about 25%, about 30%, about 35%, about 40%, about 45%, about 50%, about 55%, about 60%, about 65%, about 70%, about 75%, or greater) of Compound 1 from converting from an amorphous to a crystalline form. Stabilization can be measured, for example, by measuring the glass transition temperature of the solid dispersion, measuring the rate of relaxation of the amorphous material, or by measuring the solubility or bioavailability of Compound 1.

Suitable polymers for use in combination with Compound 1, for example to form a solid dispersion such as an amorphous solid dispersion, should have one or more of the following properties:

The glass transition temperature of the polymer should have a temperature of no less than about 10-15° C. lower than the glass transition temperature of Compound 1. Preferably, the glass transition temperature of the polymer is greater than the glass transition temperature of Compound 1, and in general at least 50° C. higher than the desired storage temperature of the drug product. For example, at least about 100° C., at least about 105° C., at least about 105° C., at least about 110° C., at least about 120° C., at least about 130° C., at least about 140° C., at least about 150° C., at least about 160° C., at least about 160° C., or greater.

The polymer should be relatively non-hygroscopic. For example, the polymer should, when stored under standard conditions, absorb less than about 10% water, for example, less than about 9%, less than about 8%, less than about 7%, less than about 6%, or less than about 5%, less than about 4%, or less than about 3% water. Preferably the polymer will, when stored under standard conditions, be substantially free of absorbed water.

The polymer should have similar or better solubility in solvents suitable for spray drying processes relative to that of Compound 1. In preferred embodiments, the polymer will dissolve in one or more of the same solvents or solvent systems as Compound 1. It is preferred that the polymer is soluble in at least one non-hydroxy containing solvent such as methylene chloride, acetone, or a combination thereof.

The polymer, when combined with Compound 1, for example in a solid dispersion or in a liquid suspension, should increase the solubility of Compound 1 in aqueous and physiologically relative media either relative to the solubility of Compound 1 in the absence of polymer or relative to the solubility of Compound 1 when combined with a reference polymer. For example, the polymer could increase the solubility of amorphous Compound 1 by reducing the amount of amorphous Compound 1 that converts to crystalline Compound 1, either from a solid amorphous dispersion or from a liquid suspension.

The polymer should decrease the relaxation rate of the amorphous substance.

The polymer should increase the physical and/or chemical stability of Compound 1.

The polymer should improve the manufacturability of Compound 1.

The polymer should improve one or more of the handling, administration or storage properties of Compound 1.

The polymer should not interact unfavorably with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound 1 or crystalline Compound 1. E.g., a candidate composition could be tested to determine whether it inhibits the time to onset of solvent mediated crystallization, or the percent conversion at a given time under controlled conditions, by at least 50%, 75%, 100%, or 110% as well as the reference preparation, or a candidate composition could be tested to determine if it has improved bioavailability or solubility relative to crystalline Compound 1.

Surfactants

A solid dispersion or other composition may include a surfactant. A surfactant or surfactant mixture would generally decrease the interfacial tension between the solid dispersion and an aqueous medium. An appropriate surfactant or surfactant mixture may also enhance aqueous solubility and bioavailability of Compound 1 from a solid dispersion. The surfactants for use in connection with the present invention include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/ hydroxystearate, Taurocholic Acid, Pluronic F68, Pluronic F108, and Pluronic F127 (or any other polyoxyethylene-polyoxypropylene co-polymers (Pluronics®) or saturated polyglycolized glycerides (Gelucirs®)). Specific example of such surfactants that may be used in connection with this invention include, but are not limited to, Span 65, Span 25, Tween 20, Capryol 90, Pluronic F108, sodium lauryl sulfate (SLS), Vitamin E TPGS, pluronics and copolymers. SLS is generally preferred.

The amount of the surfactant (e.g., SLS) relative to the total weight of the solid dispersion may be between 0.1-15%. Preferably, it is from about 0.5% to about 10%, more preferably from about 05 to about 5%, e.g., about 1%, about 2%, about 3%, about 4%, or about 5%.

In certain embodiments, the amount of the surfactant relative to the total weight of the solid dispersion is at least about 0.1, preferably about 0.5%. In these embodiments, the surfactant would be present in an amount of no more than about 15%, and preferably no more than about 12%, about 11%, about 10%, about 9%, about 8%, about 7%, about 6%, about 5%, about 4%, about 3%, about 2% or about 1%, An embodiment wherein the surfactant is in an amount of about 0.5% by weight is preferred.

Candidate surfactants (or other components) can be tested for suitability for use in the invention in a manner similar to that described for testing polymers.

Methods of Making Solid Forms of Compound 1

The solid form of Compound 1 can vary depending on the method used to prepare Compound 1. For example, Compound 1 can be prepared using a method to provide crystalline Compound 1, such as Form A or Form B, or Compound 1 can be prepared using a method to provide amorphous Compound 1, for example as a neat preparation or where Compound 1 is a component in a dispersion such as a solid amorphous dispersion (e.g., a dispersion of Compound 1 and a polymer such as a cellulosic polymer e.g., HPMC or HPMCAS or a pyrrolidone polymer such as PVP/VA).

Form A

Form A of Compound 1 can be prepared, for example, by heating Compound 1 to at or above its melting point, for example to about 250° C. and then cooling the compound, thereby providing Compound 1 having a solid state of Form A. Form A can be characterized by one or more characteristic peaks as determined using D. For example, Compound 1 as Form A can be identified by the presence of one or peaks at 2θ, including one or more of the following peaks at or about: about 5.0 e.g. 4.99; about 7.8, e.g., 7.75; about 8.5, e.g., 8.46; about 9.2, e.g., 9.21; about 9.9, e.g., 9.92; about 11.9, e.g., 11.93; about 12.6, e.g., 12.64; about 13.9, e.g., 13.88; about 14.9, e.g., 14.91; about 15.6, e.g., 15.58; about 16.5, e.g., 16.46; about 18.1, e.g., 18.09; about 18.5, e.g., 18.52; about 21.7, e.g., 20.65; about 22.0, e.g., 21.95; about 23.5, e.g., 23.49; about 25.3, e.g., 25.26; about 28.0, e.g., 28.02; about 29.4, e.g., 29.35; and about 30.9, e.g., 30.85.

Form B

Form B of Compound 1 can be prepared, for example, by subjecting a slurry of compound 1 in a solvent to heating and cooling cycles.

In some preferred embodiments, the solvent is a solvent where Compound 1 has limited solubility at room temperature, for example, acetone.

The slurry is subject to a plurality of heat/cool cycles, where the slurry is generally warmed to a temperature above room temperature but below the boiling point of the solvent, for example about 40° C. to about 60° C., e.g., about 50° C. The slurry is generally subjected to at least 2 heat/cool cycles, for example, 2, 3, 4, 5, or 6, preferably 5 cycles. Each cycle was timed to last at least about 8 hours (e.g., 4 hours of heating followed by 4 hours at room temperature, 6 hours of heating followed by 6 hours at room temperature, 8 hours of heating followed by 8 hours at room temperature, preferably 12 hours of heating followed by 12 hours at room temperature).

In an alternative embodiment crude Compound 1 can be refluxed in as a slurry in acetonitrile (e.g., 27 volumes of acetonitrile) for 24 hours. The mixture is then cooled, e.g., to about room temperature, e.g., about 20° C. Form B is then isolated, for example, by filtration as a white to off-white. The resulting wet cake is rinsed with acetonitrile (e.g., 5 volumes) and dried under vacuum at 50° C. until a constant weight is attained.

Form B can be characterized by one or more characteristic peaks as determined using XRPD. For example, Compound 1 as Form B can be identified by the presence of one or peaks at 2θ, including one or more of the following peaks at or about: about 6.2, e.g., 6.17; about 7.6, e.g., 7.61; about 8.4, e.g., 8.40; about 11.0, e.g., 11.02; about 12.3, e.g., 12.33; about 14.8, e.g., 14.83; about 16.1, e.g., 16.14; about 17.1, e.g., 17.11; about 18.0, e.g., 17.96; about 18.6, e.g., 18.55; about 19.4, e.g., 19.43; about 21.1, e.g., 21.05; about 22.6, e.g., 22.56; about 23.4, e.g., 23.37; about 23.9, e.g., 23.94; about 24.9, e.g., 24.86; about 25.5, e.g., 25.50; about 26.7, e.g., 26.72; about 27.5, e.g., 27.51; about 29.6, e.g., 29.60; about 33.5, e.g., 33.48; and about 36.8, e.g., 36.78.

Amorphous Compound 1

Amorphous compound 1 can be made using a variety of techniques, including, for example spray drying a solution of Compound 1 to provide amorphous Compound 1, e.g., as a neat solid or as a component of a solid dispersion, said method utilizing spray-drying means to effect said conversion. For example, Amorphous Compound 1 can be made by converting a form of Compound 1, e.g., a crystalline form of Compound 1, such as Form A or Form B, into a substantially amorphous form of Compound 1 by dissolving Compound into a solution and spray drying the solution of Compound 1, thereby converting a form of Compound 1, such as crystalline Compound 1, into amorphous Compound 1. An exemplary process for making amorphous Compound 1 by converting Form B into a substantially amorphous form of Compound 1 is recited in the examples.

Any method for obtaining amorphous forms of Compound 1, including neat amorphous Compound 1 and solid amorphous dispersions of Compound 1, can be used including, for example, those described in US 2003/0186952 (see the documents cited therein at paragraph 1092) and US 2003/0185891). In general, methods that could be used include those that involve rapid removal of solvent from a mixture or cooling a molten sample. Such methods include, but are not limited to, rotational evaporation, freeze-drying (i.e., lyophilization), vacuum drying, melt congealing, and melt extrusion. However, a preferred embodiment includes amorphous Compound 1, such as a neat preparation or a solid dispersion obtained by spray drying. Accordingly, in some embodiments, the amorphous product obtained by spray-drying is further dried, for example, to remove residual solvent.

Preparations disclosed herein, e.g., a pharmaceutical composition, can be obtained by spray-drying a mixture comprising Compound 1, a suitable polymer, and an appropriate solvent. Spray drying is a method that involves atomization of a liquid mixture containing, e.g., a solid and a solvent, and removal of the solvent. Atomization can be done, for example, through a nozzle or on a rotating disk.

Spray drying is a process that converts a liquid feed to a dried particulate form. Optionally, a secondary drying process such as fluidized bed drying or vacuum drying, may be used to reduce residual solvents to pharmaceutically acceptable levels. Typically, spray-drying involves contacting a highly dispersed liquid suspension or solution, and a sufficient volume of hot air to produce evaporation and drying of the liquid droplets. The preparation to be spray dried can be any solution, coarse suspension, slurry, colloidal dispersion, or paste that may be atomized using the selected spray-drying apparatus. In a standard procedure, the preparation is sprayed into a current of warm filtered air that evaporates the solvent and conveys the dried product to a collector (e.g., a cyclone). The spent air is then exhausted with the solvent, or alternatively the spent air is sent to a condenser to capture and potentially recycle the solvent. Commercially available types of apparatus may be used to conduct the spray-drying. For example, commercial spray dryers are manufactured by Buchi Ltd. and Niro (e.g., the PSI) line of spray driers manufactured by Niro) (see, US 2004/0105820; US 2003/0144257).

Spray-drying typically employs solids loads of material from about 3% to about 30% by weight, (i.e., drug plus and excipients), for example about 4% to about 20% by weight, preferably at least about 10%. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954). In general, the spray-drying is conducted with an inlet temperature of from about 60° C. to about 200° C., for example, from about 95° C. to about 185° C., from about 110° C. to about 182° C., from about 96° C. to about 108° C., e.g., about 175° C., The spray-drying is generally conducted with an outlet temperature of from about 30° C. to about 80° C., for example from about 31° C. to about 72° C., about 37° C. to about 41° C. e.g., about 60° C. The atomization flow rate is generally from about 4 kg/h to about 12 kg/h, for example, from about 4.3 kg/h to about 10.5 kg/h, e.g., about 6 kg/h or about 10.5 kg/h. The feed flow rate is generally from about 3 kg/h to about 10 kg/h, for example, from about 3.5 kg/h to about 9.0 kg/h, e.g., about 8 kg/h or about 7.1 kg/h. The atomization ratio is generally from about 0.3 to 1.7, e.g., from about 0.5 to 1.5, e.g., about 0.8 or about 1.5.

Removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the solid dispersion is fluid-bed dried.

In preferred processes, the solvent includes a volatile solvent, for example a solvent having a boiling point of less than about 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than about 15%, e.g., less than about 12%, less than about 10%, less than about 8%, less than about 5%, less than about 3%, or less than about 2%.

Preferred solvents are those solvents where Compound 1 has a solubility of at least about 10 mg/nil (e.g., at least about 15 mg/ml, 20 mg/ml, 25 mg/ml, 30 mg/ml, 35 mg/ml, 40 mg/ml, 45 mg/ml, 50 mg/ml, or greater). More preferred solvents include those where Compound 1 has a solubility of at least about 50 mg/ml.

Exemplary solvents that could be tested include acetone, cyclohexane, dichloromethane, N,N-Dimethylacetamide (DMA), N,N-Dimethylformamide (DMF), 1,3 Dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether, tetrahydrofuran (THF) and pentane. Exemplary co-solvents include acetone/DMSO, acetone/DMF, acetone/water, MEK/water, THF/water, dioxane/water. In a two solvent system, the solvents can be present in of from about 0.1% to about 99.9%. In some preferred embodiments, water is a co-solvent with acetone where water is present from about 0.1% to about 15%, for example about 9% to about 11%, e.g., about 10%. In some preferred embodiments, water is a co-solvent with MEK where water is present from about 0.1% to about 15%, for example about 9% to about 11%, e.g., about 10%. In some embodiments the solvent solution include three solvents. For example, acetone and water can be mixed with a third solvent such as DMA, DMF, DMI, DMSO, or HAc. In instances where amorphous Compound 1 is a component of a solid amorphous dispersion, preferred solvents dissolve both Compound 1 and the polymer. Suitable solvents include those described above, for example, MEK, acetone, water, and mixtures thereof.

The particle size and the temperature drying range may be modified to prepare an optimal solid dispersion. As would be appreciated by skilled practitioners, a small particle size would lead to improved solvent removal. Applicants have found however, that smaller particles can lead to fluffy particles that, under some circumstances do not provide optimal solid dispersions for downstream processing such as tabletting. At higher temperatures, crystallization or chemical degradation of Compound 1 may occur. At lower temperatures, a sufficient amount of the solvent may not be removed. The methods herein provide an optimal particle size and an optimal drying temperature.

In general, particle size is such that D10 (μm) is less than about 5, e.g., less than about 4.5, less than about 4.0, or less than about 3.5, D50 (μm) is generally less than about 17, e.g., less than about 16, less than about 15, less than about 14, less than about 13, and 1390 (μm) is generally less than about 175, e.g., less than about 170, less than about 170, less than about 150, less than about 125, less than about 100, less than about 90, less than about 80, less than about 70, less than about 60, or less than about less than about 50. In general bulk duty of the spray dried particles is from about 0.08 g/cc to about 0.20 g/cc, e.g., from about 0.10 to about 0.15 g/cc, e.g., about 0.11 g/cc or about 0.14 g/cc. Tap density of the spray dried particles generally ranges from about 0.08 g/cc to about 0.20 g/cc, e.g., from about 0.10 to about 0.15 g/cc, e.g., about 0.11 g/cc or about 0.14 g/cc, for 10 taps; 0.10 g/cc to about 0.25 g/cc, e.g., from about 0.11 to about 0.21 g/cc, e.g., about 0.15 g/cc, about 0.19 g/cc, or about 0.21 g/cc for 500 taps; 0.15 g/cc to about 0.27 g/cc, e.g., from about 0.18 to about 0.24 g/cc, e.g., about 0.18 g/cc, about 0.19 g/cc, about 0.20 g/cc, or about 0.24 g/cc for 1250 taps; and 0.15 g/cc to about 0.27 g/cc, e.g., from about 0.18 to about 0.24 g/cc, e.g., about 0.18 g/cc, about 0.21 g/cc, about 0.23 g/cc, or about 0.24 g/cc for 2500 taps.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. All tautomeric forms of the Compound 1 are included herein. E.g., Compound 1 may exist as tautomers, both of which are included herein:

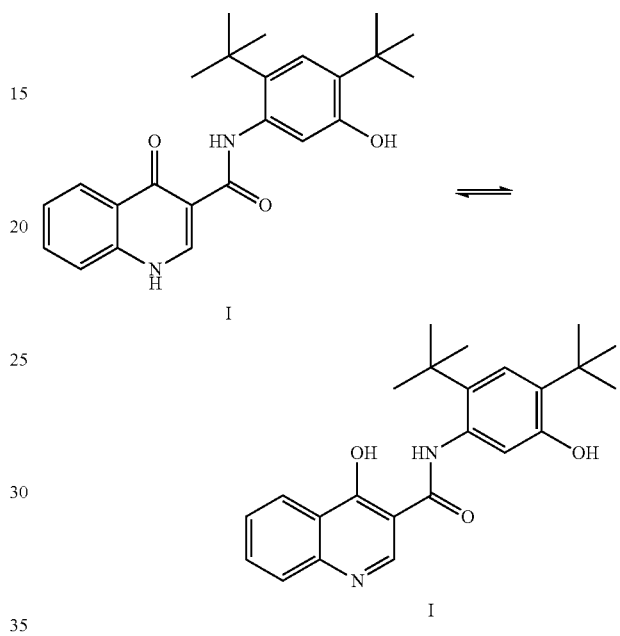

Additionally, unless otherwise stated, structures depicted herein are also meant to include compounds that differ only in the presence of one or more isotopically enriched atoms. For example, compounds of formula (I), wherein one or more hydrogen atoms are replaced deuterium or tritium, or one or more carbon atoms are replaced by a 13C- or 14C-enriched carbon are within the scope of this invention. Such compounds are useful, for example, as analytical tools, probes in biological assays, or compounds with improved therapeutic profile.

Uses, Formulation and Administration

Pharmaceutically Acceptable Compositions

In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-49, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E, W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by cm. In certain embodiments, the present invention provides a method of treating a condition, disease, or disorder implicated by a deficiency of CFTR activity, the method comprising administering a composition comprising a solid state form of Compound 1 described herein (e.g., Form A, Form B, or amorphous Compound 1, e.g., neat or as a component in a dispersion) to a subject, preferably a mammal, in need thereof.

A "CFTR-mediated disease" as used herein is a disease selected from cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type H, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type 1, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Seheinker syndrome, COPD, dry-eye disease, and Sjogren's disease.

In certain embodiments, the present invention provides a method of treating cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, comprising the step of administering to said mammal an effective amount of a composition comprising a solid state form of Compound 1 described herein (e.g., Form A, or Form B, or amorphous Compound 1, e.g., neat or as a component in a dispersion).

According to an alternative preferred embodiment, the present invention provides a method of treating cystic fibrosis comprising the step of administering to said mammal a composition comprising a solid state form of Compound 1 described herein (e.g., Form A, or Form B, or amorphous Compound 1, e.g., neat or as a component in a dispersion).

According to the invention an "effective amount" of a solid state form of Compound 1 (e.g., Form A, or Form B, or amorphous Compound 1, e.g., neat or as a component in a dispersion) or a pharmaceutically acceptable composition thereof is that amount effective for treating or lessening the severity of any of the diseases recited above.

A solid state form of Compound 1 (e.g., Form A, or Form B, or amorphous Compound 1, e.g., neat or as a component in a dispersion) or a pharmaceutically acceptable composition thereof may be administered using any amount and any route of administration effective for treating or lessening the severity of one or more of the diseases recited above.

In certain embodiments, a solid state form of Compound 1 described herein (e.g., Form A, or Form B, or amorphous Compound 1, e.g., neat or as a component in a dispersion) or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex viva electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In one embodiment, a solid state form of Compound 1 described herein (e.g., Form A, or Form B, or amorphous Compound 1, e.g., neat or as a component in a dispersion) or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy;* Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, a solid state form of Compound 1 described herein (e.g., Form A, or Form B, or amorphous Compound 1, e.g., neat or as a component in a dispersion) or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, micro emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfide, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body.

Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the solid state form of Compound 1 described herein (e.g., Form A, or Form B, or amorphous Compound 1, e.g., neat or as a component in a dispersion) or a pharmaceutically acceptable composition thereof can be employed in combination therapies, that is, Form A or Form B or a pharmaceutically acceptable composition thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodilator, an anti-biotic, an anti-infective agent, an anti-inflammatory agent, a CFTR modulator other than a compound of the present invention, or a nutritional agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

A solid state form of Compound 1 described herein (e.g., Form A, or Form B, or amorphous Compound 1, e.g., neat or as a component in a dispersion) or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising a solid state form of Compound 1 described herein (e.g., Form A, or Form B, or amorphous Compound 1, e.g., neat or as a component in a dispersion) or a pharmaceutically acceptable composition thereof, and a carrier suitable for coating said implantable device. In still another aspect, the present invention includes an implantable device coated with a composition comprising a solid state form of Compound 1 described herein (e.g., Form A, or Form B, or amorphous Compound 1, e.g., neat or as a component in a dispersion) or a pharmaceutically acceptable composition thereof, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

In order that the invention described herein may be more fully understood, the following examples are set forth. It should be understood that these examples are for illustrative purposes only and are not to be construed as limiting this invention in any manner.

EXAMPLES

Methods & Materials

Differential Scanning Calorimetry (DSC)

The Differential scanning calorimetry (DSC) data of Form A, Form B, and amorphous Compound 1 were collected using a DSC Q100 V9.6 Build 290 (TA Instruments, New Castle, Del.). Temperature was calibrated with indium and heat capacity was calibrated with sapphire. Samples of 3-6 mg were weighed into aluminum pans that were crimped using lids with 1 pin hole. The samples were scanned from 25° C. to 350° C. at a heating rate of 10° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent single analyses.

Thermogravimetric Analysis (TGA).

Thermal gravimetric analysis (TGA) was performed with a TGA Q500 V6.3 Build 189 (TA Instruments, New Castle, Del.) was used for TGA measurement. Temperature was equilibrated by Curie point with nickel. Samples of 10-20 mg were scanned from 25° C. to 350° C. at a heating rate of 10° C./min. A nitrogen gas balance purge of 10 ml/min and a sample purge of 90 ml/min were used. Data were collected by Thermal Advantage Q Series™ software version 2.2.0.248 and analyzed by Universal Analysis software version 4.1D (TA Instruments, New Castle, Del.). The reported numbers represent single analyses.

XRPD (X-Ray Powder Diffraction)

The X-Ray diffraction (XRD) data of Form A, Form B, and amorphous Compound 1 were collected on a Bruker D8 DISCOVER with GADDS powder diffractometer with HI-STAR 2-dimensional detector and a flat graphite monochromator. Cu sealed tube with Kα radiation was used at 40 kV, 35 mA. The samples were placed on zero-background silicon wafers at 25° C., For each sample, two data frames were collected at 120 seconds each at 2 different 2θ angles: 8° and 26°. The frames data were integrated with GADDS software and merged with DIFFRACT$^{plus}$ EVA software.

Synthesis of N-[2,4-bis(1,1-dimethylethyl)-5-hydroxyphenyl]-1,4-dihydro-4-oxoquinoline-3-carboxamide (Compound 1)

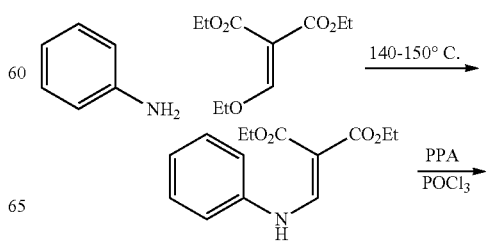

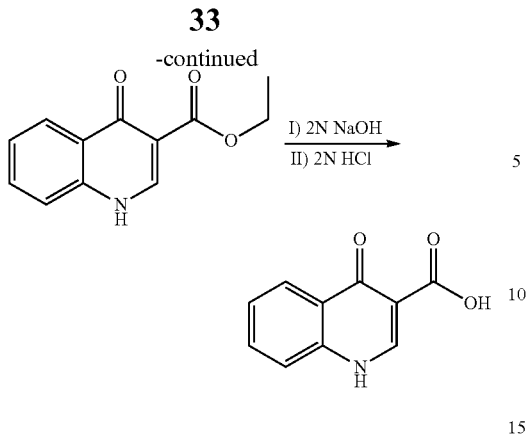

2-Phenylaminomethylene-malonic Acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. $^1$H NMR (DMSO-4) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

4-Hydroxyquinoline-3-carboxylic Acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na$_2$CO$_3$ solution, filtered, washed with water and dried, 4-hydroxyquinoline-3-carboxylic acid ethyl ester was obtained as a pale brown solid (15.2 g, 70%). The crude product was used in next step without further purification.

4-Oxo-1,4-dihydroquinoline-3-carboxylic Acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%), $^1$H NMR (DMSO-d$_6$) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

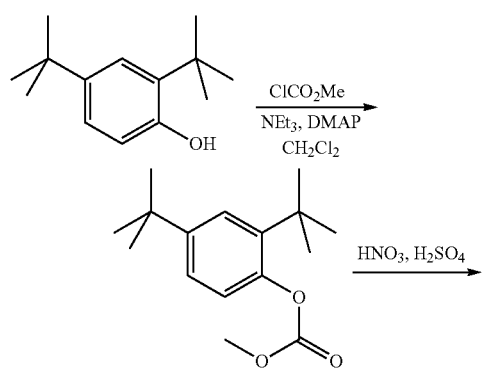

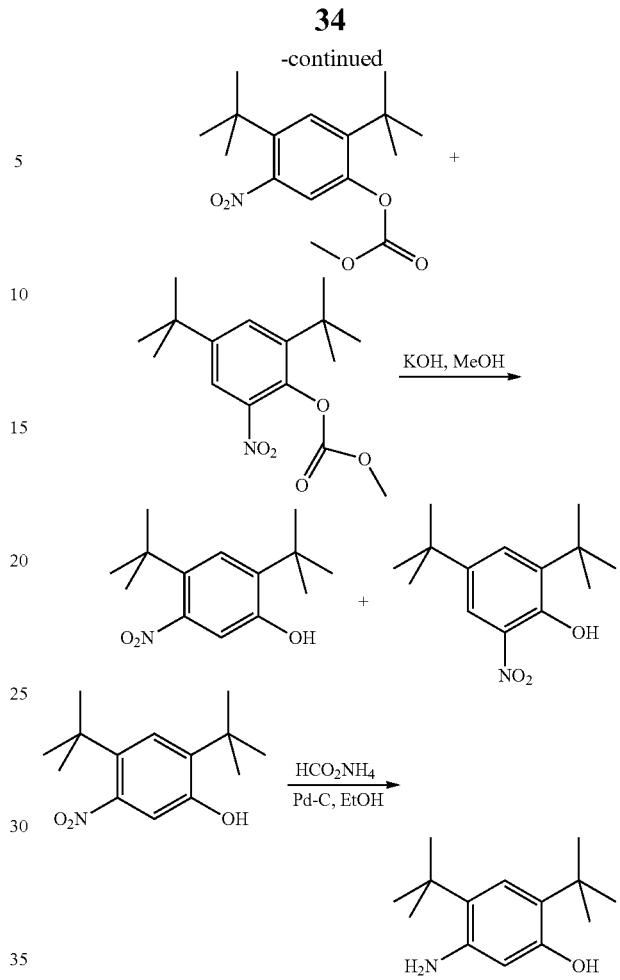

Carbonic Acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et$_3$N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d$_6$) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Carbonic Acid 24-di-tert-butyl-5-nitro-phenyl ester methyl ester and Carbonic Acid 2,4-di-tertbutyl-6-nitro-phenyl ester methyl ester To a stirring mixture of carbonic acid 2,4-di-ten-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO₄), concentrated and purified by column chromatography (0-10% ethyl acetate hexanes) to yield a mixture of carbonic acid 2,4-di-tert butyl-5-nitro phenyl ester methyl ester and carbonic acid 2,4-di-tert-butyl-6-nitro-phenyl ester methyl ester as a pale yellow solid (4.28 g), which was used directly in the next step.

2,4-Di-tert-butyl-5-nitro-phenol and 2,4-Di-tert-butyl-6-nitro-phenol

The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO₄), concentrated and purified by column chromatography (0-5% ethyl acetate-hexanes) to provide 2,4-di-tert-butyl-5-nitro-phenol (1.31 g, 29% over 2 steps) and 2,4-di-tertbutyl-6-nitro-phenol. 2,4-Di-tert-butyl-5-nitro-phenol: $^1$H NMR (400 MHz, DMSO-$d_6$) δ 10.14 (s, 1H, OH), 7.34 (s, 1H), 6.83 (s, 1H), 1.36 (s, 9H), 1.30 (s, 9H), 2,4-Di-tert-butyl-6-nitro-phenol: $^1$H NMR (400 MHz, CDCl₃) δ 11.48 (s, 1H), 7.98 (d, J=2.5 Hz, 1H), 7.66 (d, J=2.4 Hz, 1H), 1.47 (s, 9H), 1.34 (s, 9H).

5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-$d_6$) δ 8.64 (s, 1H, OH), 6.84 (s, 1H), 6.08 (s, 1H), 4.39 (s, 2H, NH₂), 1.27 (m, 18H); HPLC ret. time 2.72 min, 1099% CH₃CN, 5 min run; ESI-MS 222.4 ink [M+H]⁺.

N-[2,4-bis(1,1-dimethylethyl)-5-hydroxyphenyl]-1,4-dihydro-4-oxoquinoline-3-carboxamide

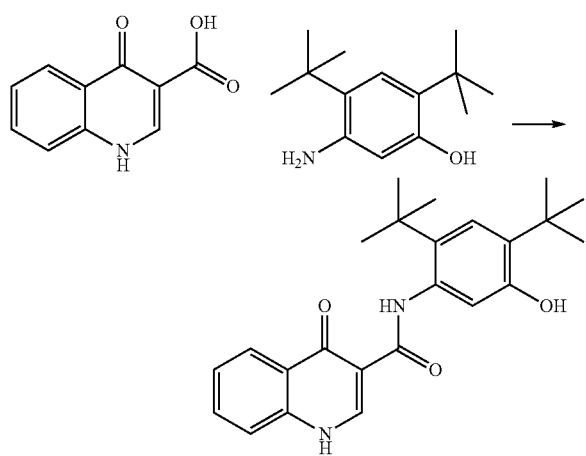

To a suspension of 4-oxo-1,4-dihydroquinolin-3-carboxylic acid (35.5 g, 188 mmol) and HBTU (85.7 g, 226 mmol) in DMF (280 mL) was added Et₃N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo, EtOH was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. Et₂O was added to the material obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide 8 N-[2,4-bis(1,1-dimethylethyl)-5-hydroxyphenyl]-1,4-dihydro-4-oxoquinoline-3-carboxamide as a white powdery solid (38 g, 52%).

HPLC ret. time 3.45 min, 10-99% CH₃CN, 5 rain run; $^1$H NMR (400 MHz, DMSO-$d_6$) δ 12.88 (s, 1H), 11.83 (s, 1H), 9.20 (s, 1H), 8.87 (s, 1H), 8.33 (dd, 0.1=8.2, 1.0 Hz, 1H), 7.83-7.79 (m, 1H), 7.76 (d, J=7.7 Hz, 1H), 7.54-7.50 (m, 1H), 7.17 (s, 1H) 7.10 (s, 1H), 1.38 (s, 9H), 1.37 (s, 9H); ESI-MS 393.3 m/z [M+H]⁺.

Set forth below is the characterizing data for Compound 1;

TABLE 2

| Cmd No. | LC-MS M + 1 | LC-RT min |
|---|---|---|
| 1 | 393.2 | 3.71 |

Figure 2:
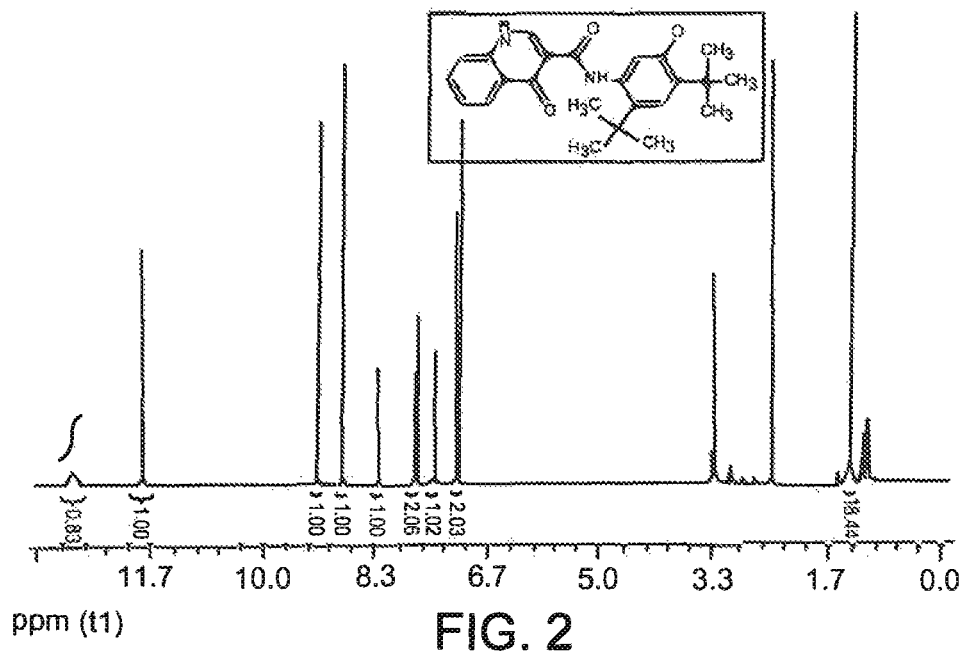
FIG. 2 is the $^1$H NMR spectrum of Compound 1.
Figure 3:
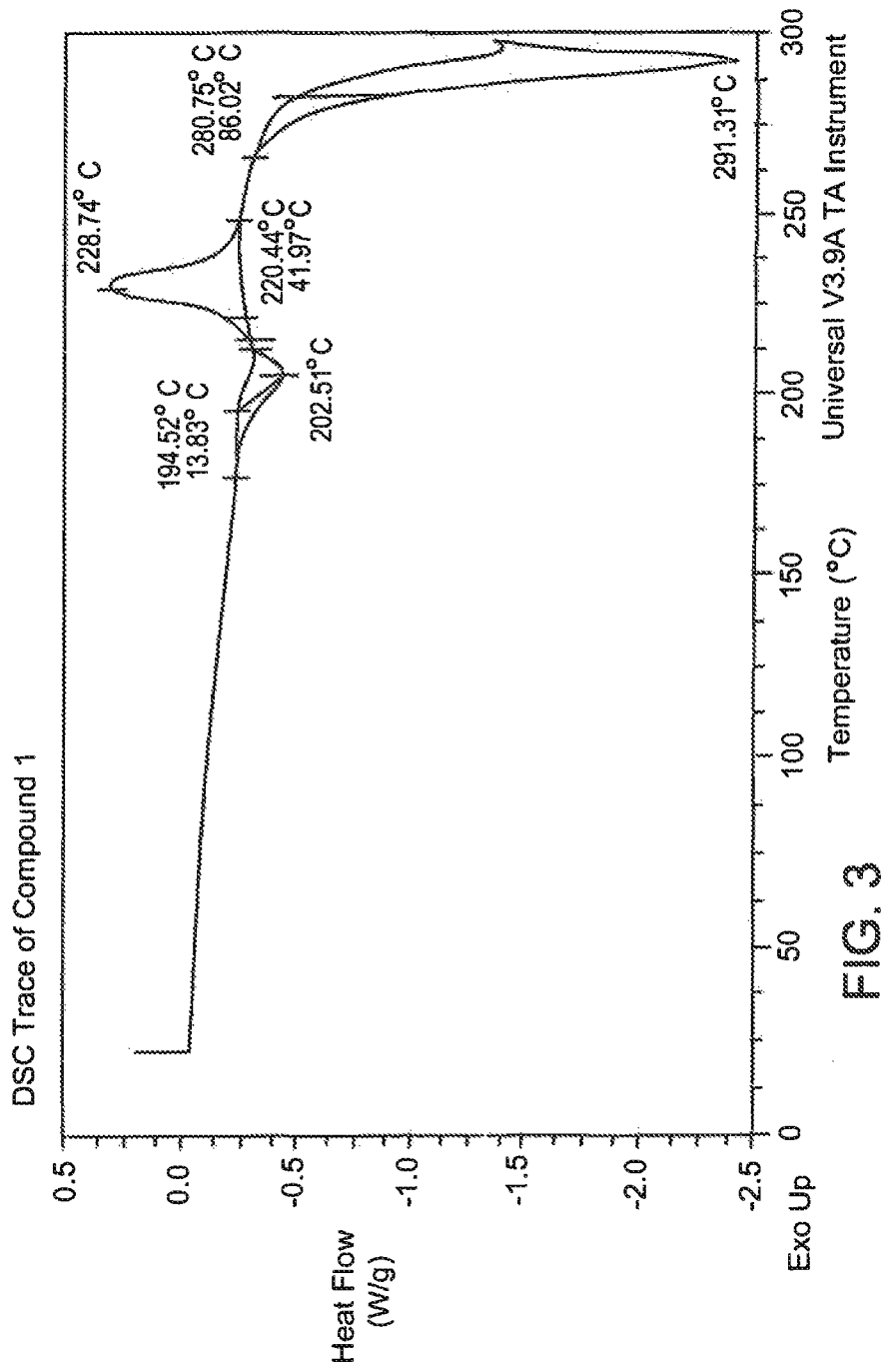
FIG. 3 is the DSC trace of Compound 1.

The XRPD spectrum of Compound 1 is shown in FIG. 1. $^1$H NMR data for Compound 1 in shown in FIG. 2. The DSC trace of Compound 1 is shown in FIG. 3.

Preparation of Form A

Form A was obtained by heating Compound 1 as a solid to 250° C. and cooling to room temperature. The DSC thermogram on Compound 1 (See FIG. 6) shows that the compound undergoes a melt with an onset temperature of 195° C., followed by a re-crystallisation with onset at 220° C.

Figure 4:
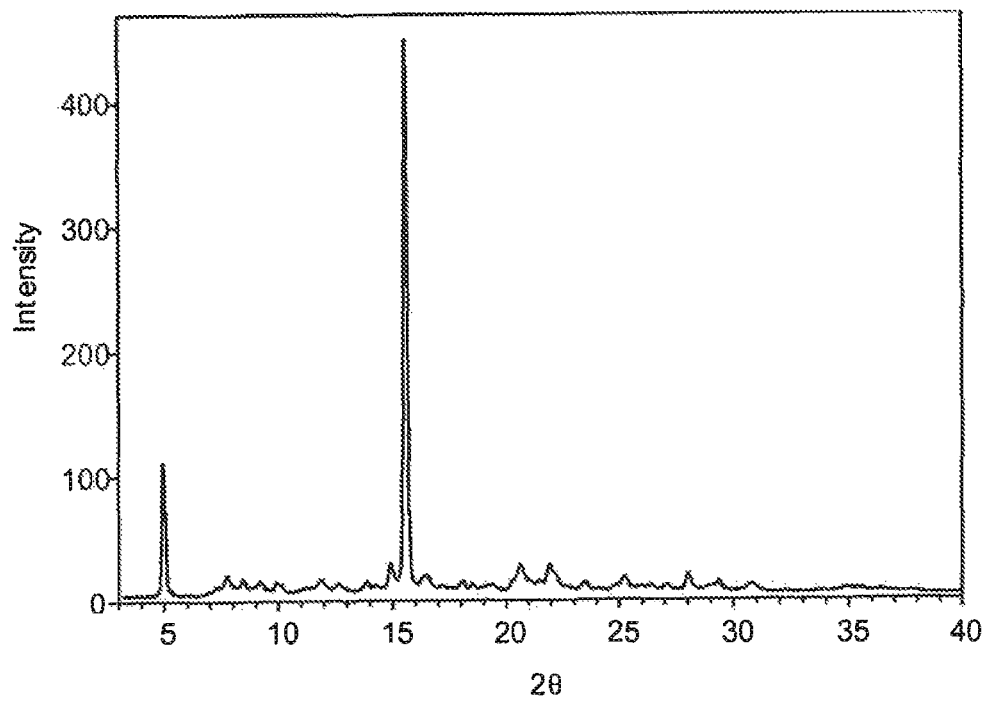
FIG. 4 is the X-Ray powder diffraction pattern of Form A.
Figure 5:
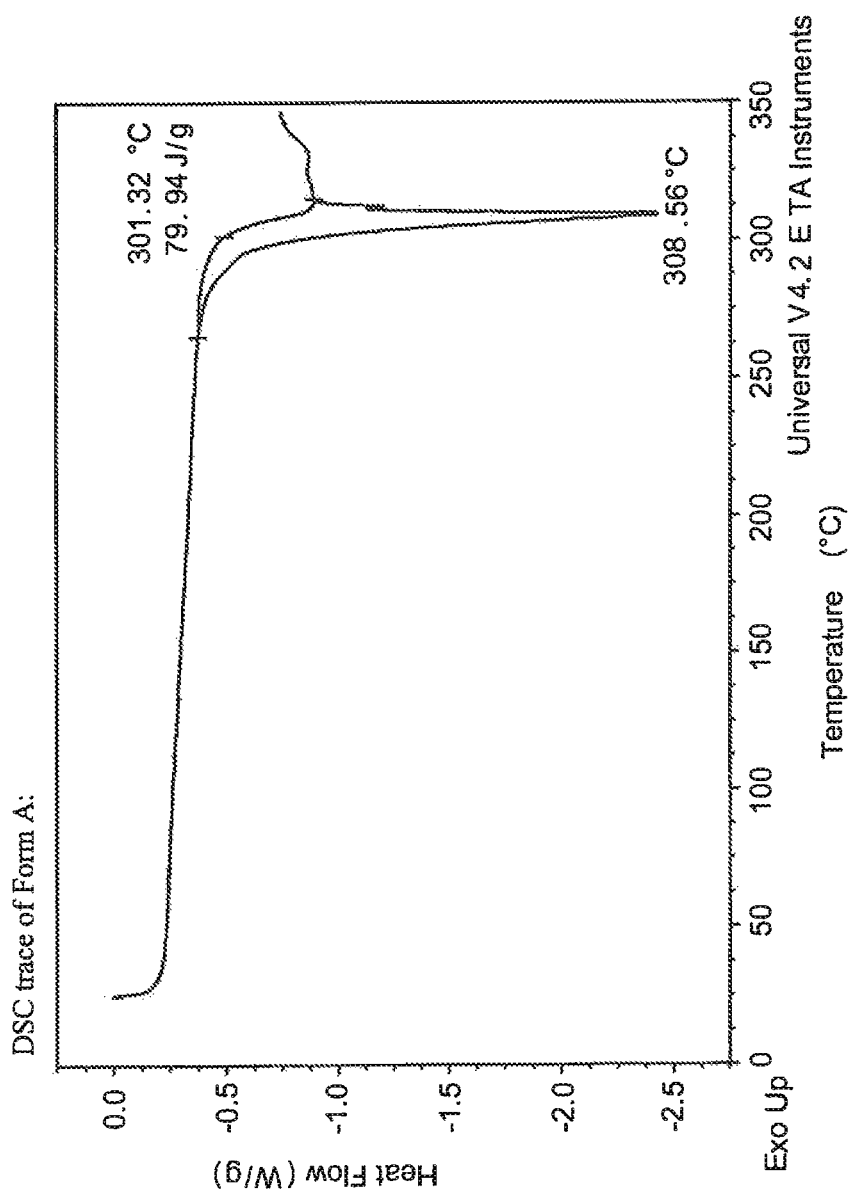
FIG. 5 is the DSC trace of Form A.
Figure 6:
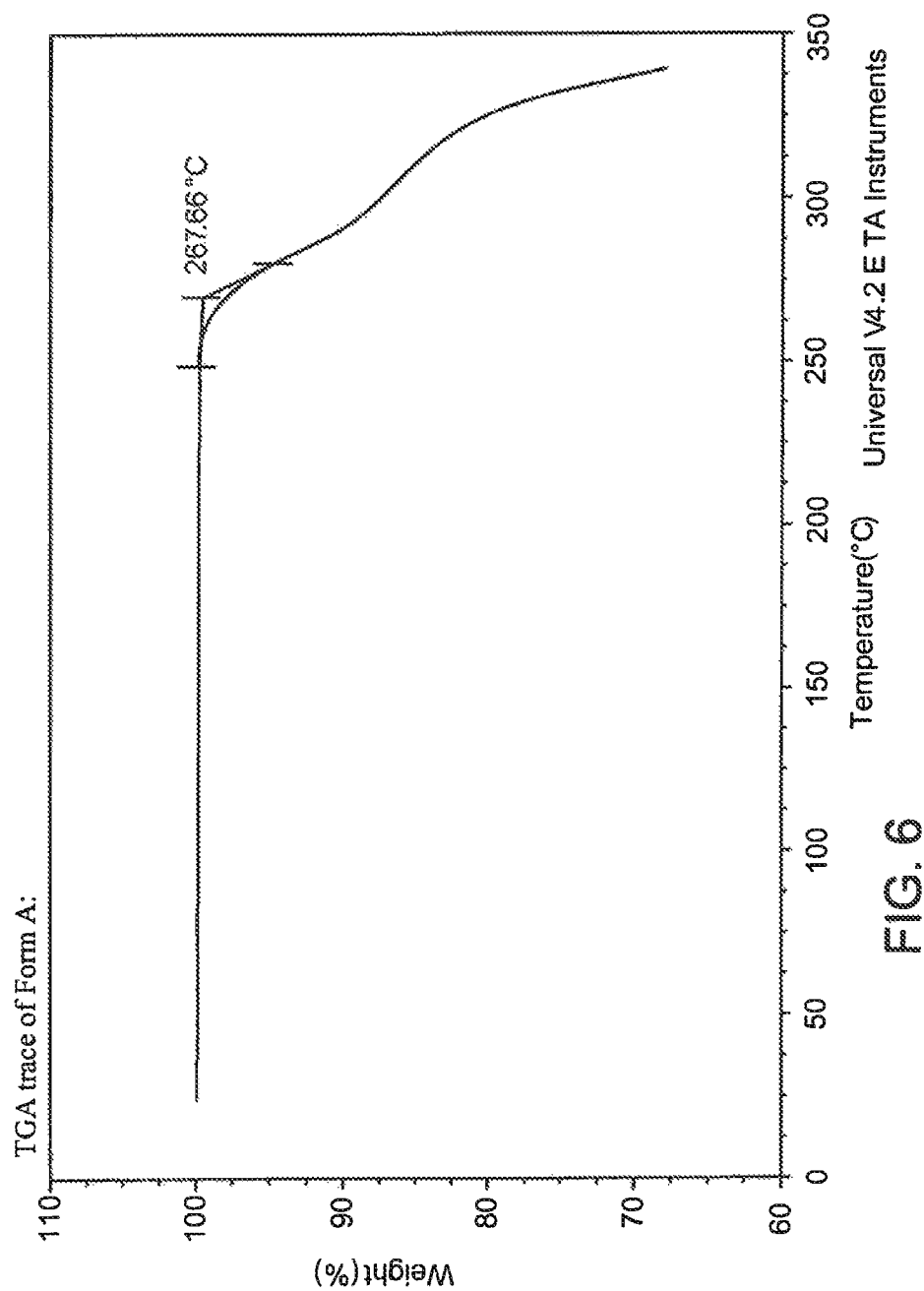
FIG. 6 is the TGA trace of Form A.

The XRPD spectrum of Form A is shown in FIG. 4.
The DSC data for Form A is shown in FIG. 5.
The TGA trace for Form A is shown in FIG. 6.

Preparation of Form B

Crude Compound 1 was a slurry in refluxing acetonitrile (27 volumes) for 24 hours. After 24 hours, the mixture was allowed to cool to 20° C. Form B was isolated by filtration as a white to off-white. The wet cake was rinsed with acetonitrile (5 volumes) and dried under vacuum at 50° C. until a constant weight is attained, thereby providing Form B.

Figure 7:
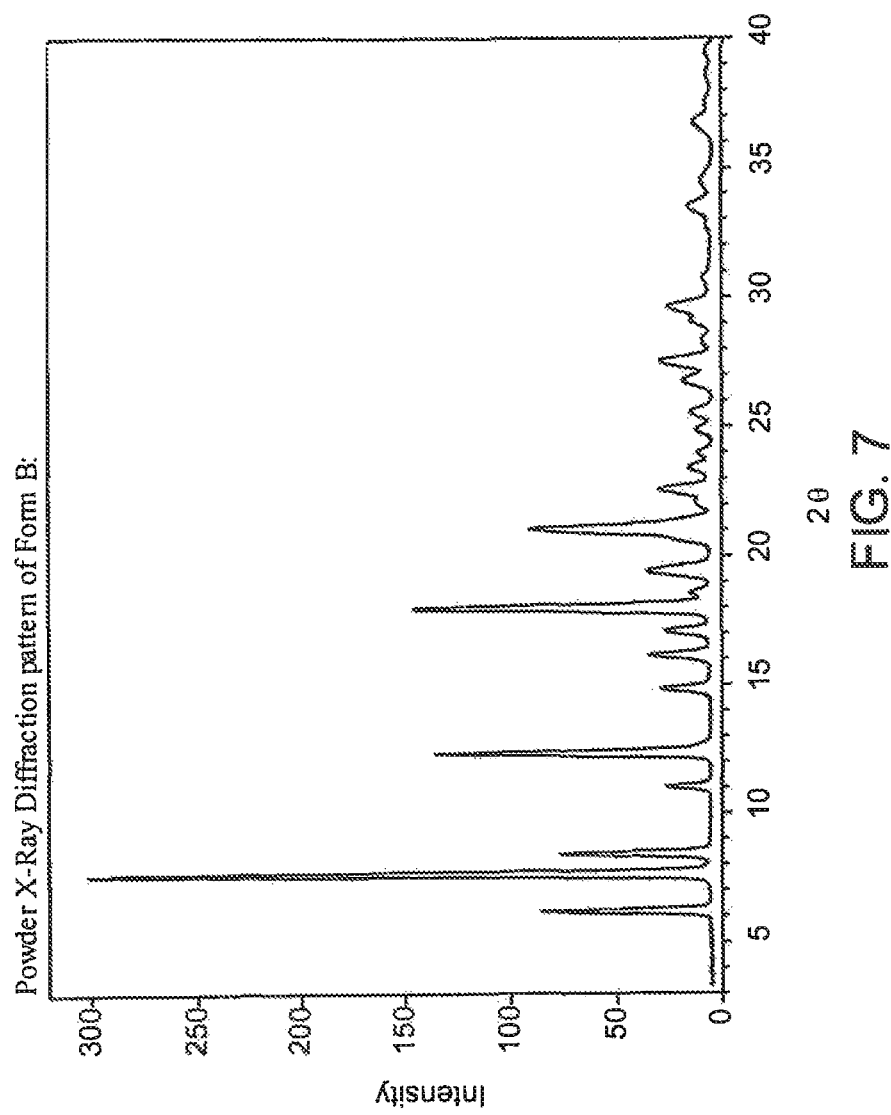
FIG. 7 is the X-Ray powder diffraction pattern of Form B.
Figure 8:
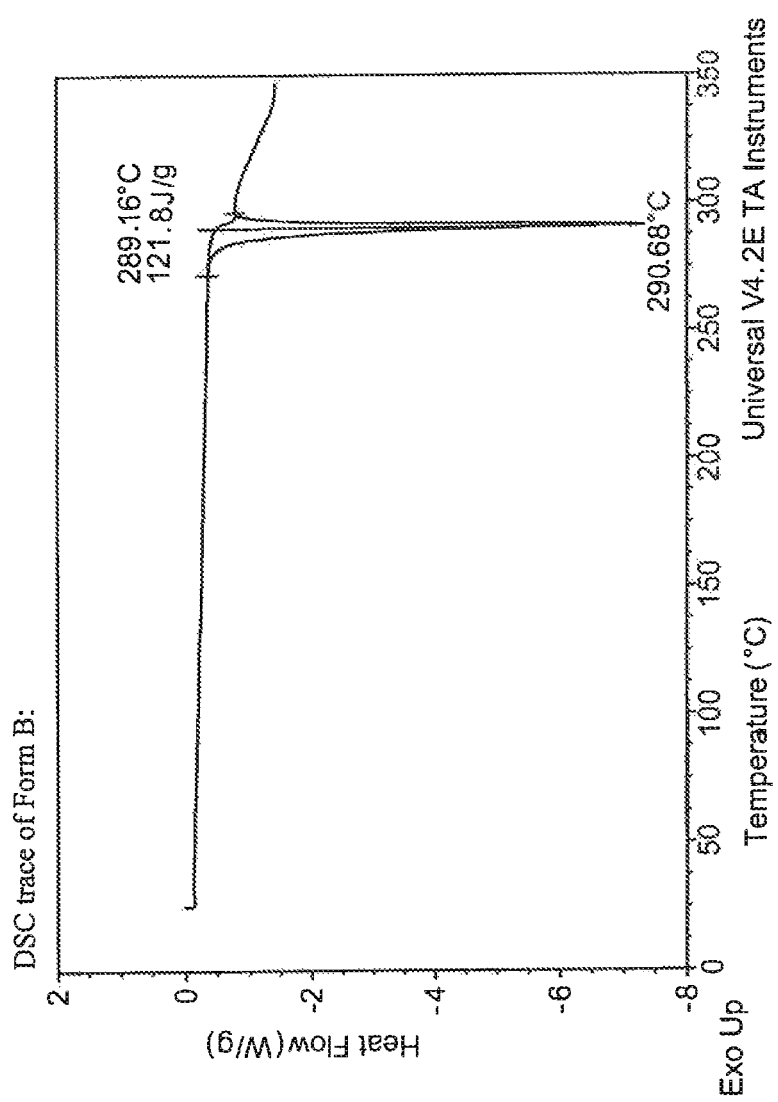
FIG. 8 is the DSC trace of Form B.
Figure 9:
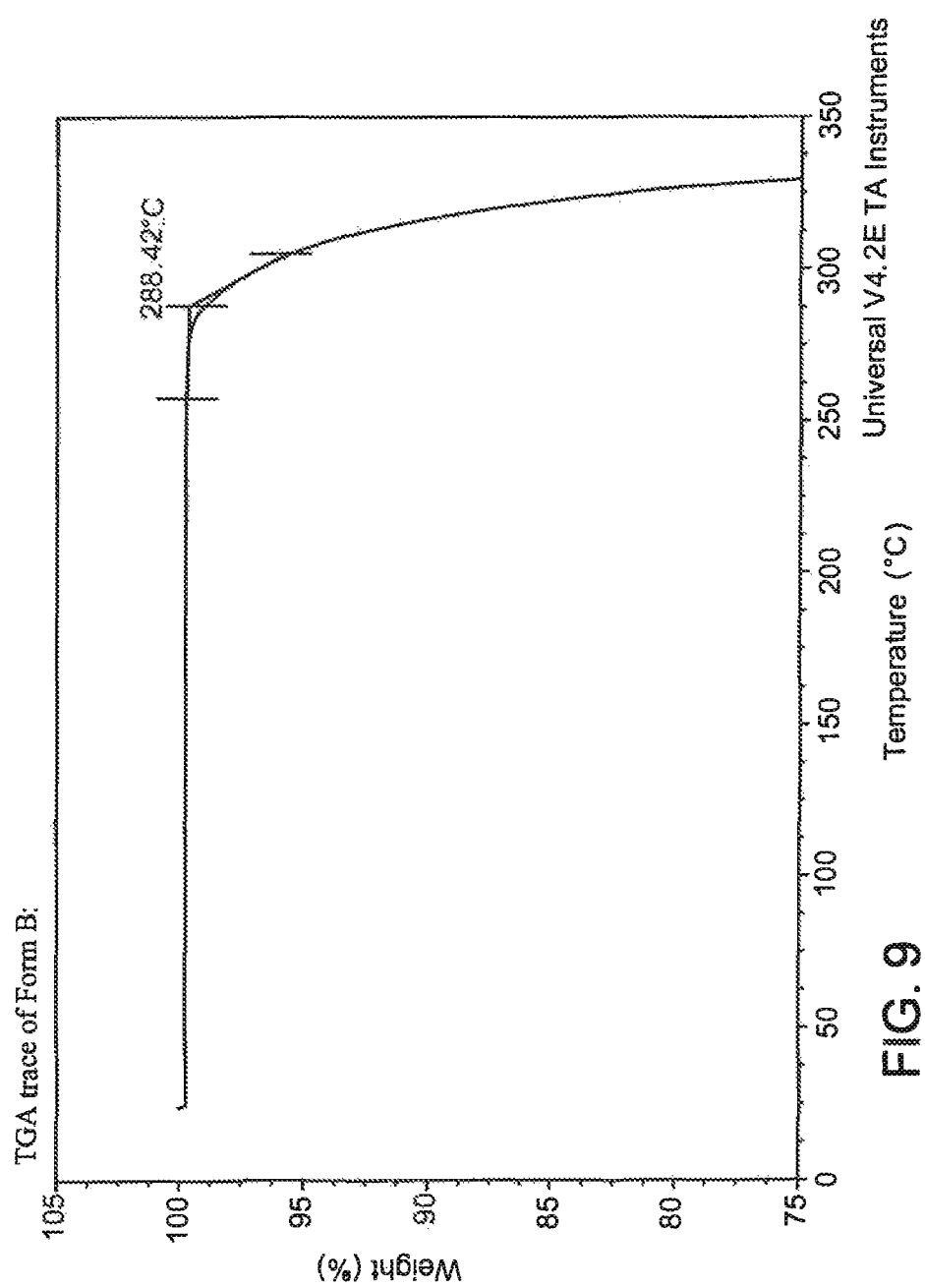
FIG. 9 is the TGA trace of Form B.

The XRPD spectrum of Form B is shown in FIG. 7.
The DSC trace of Form B is shown in FIG. 8.
The TGA trace for Form B is shown in FIG. 9.

Single crystal data was obtained for Form B, providing detail additional detail about the crystal structure, including lattice size and packing.

Crystal Preparation:

1 g of Compound 1 was added to 10 ml of isopropanol acetate. The suspension was heated and remained at 60° C. for 3 hours. The suspension was cooled to room temperature and remained stirred overnight. The suspended solid was filtered and washed with isopropanol acetate. The collected solid was dried under vacuum at room temperature. 300 mg of the dried solid was dissolved in 5 ml of 10% aqueous ethyl acetate solution. The solution was heated to 70° C. for 10 minutes before it was cooled to room temperature. Over time, crystals grew in the vial.

EXPERIMENTAL

A single crystal of Form B was mounted on a MicroMount loop and centered on a Bruker Apex II diffractometer that was equipped with a sealed copper X-ray tube and Apex II CCD detector. Initially, 3 sets of 40 frames were collected to determine a preliminary unit cell. Subsequently a full data set consisting of 15 scans and 6084 frames was acquired. Data collection was performed at 100 K. Data were integrated and scaled using Apex II software from Braker AXS. Integration and scaling resulted in 7528 reflections, 3071 of which were unique [R(int))=0.0466]. Structure was solved by direct methods in space group $P2_1$ using SHELXTL software. Refinement was performed with full-matrix least-square method on $F^2$ using SHELXTL, software as well. Altogether 375 parameters were used in refinement resulting in reflection to parameter ratio of 8.19. The final refinement afforded a chiral structure with a Flack parameter of 0.0(3). The final refinement index was wR2=0.1242 and R1=0.0663 (wR2=0.1137 and R1=0.0482 for reflections with I>2 sigma (I)).

Figure 10:
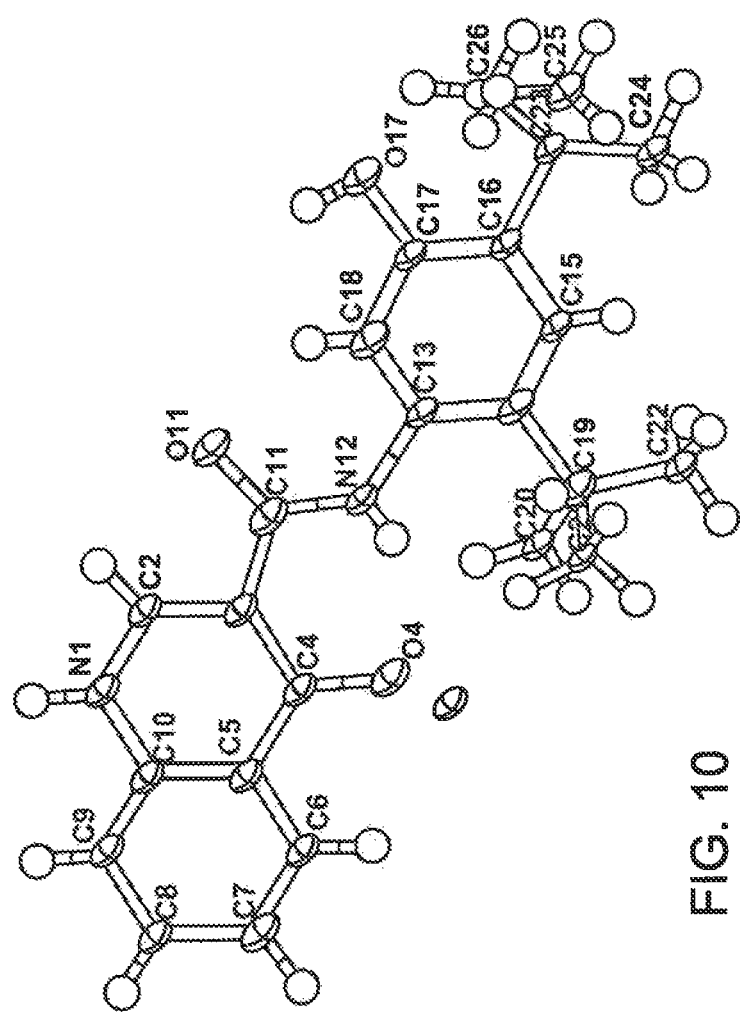
FIG. 10 is a conformational picture of Form B, based on single crystal X-Ray analysis.

A conformational picture of Form B is provided in FIG. 10, which is in color.

TABLE 1

Crystal data and structure refinement for Compound 1.

| Identification code | Compound 1 |
|---|---|
| Empirical formula | C24 H28 N2 O3 |
| Formula weight | 392.48 |
| Temperature | 100(2) K |
| Wavelength | 1.54178 Å |
| Crystal system | monoclinic |
| Space group | $P2_1$ |
| Unit cell dimensions | a = 11.8011(7) Å    α = 90°. |
|  | b = 5.9819(3) Å    β = 105.110(4)°. |
|  | c = 14.7974(8) Å    γ = 90°. |
| Volume | 1008.48(10) Å$^3$ |
| Z | 2 |
| Density (calculated) | 1.293 Mg/m$^3$ |
| Absorption coefficient | 0.681 mm$^{-1}$ |
| F(000) | 420 |
| Crystal size | 0.20 × 0.08 × 0.08 mm$^3$ |
| Theta range for data collection | 3.09 to 68.67°. |
| Index ranges | −14 <= h <= 14, −7 <= k <= 7, −14 <= l <= 17 |

TABLE 1-continued

Crystal data and structure refinement for Compound 1.

| Identification code | Compound 1 |
|---|---|
| Reflections collected | 7528 |
| Independent reflections | 3071 [R(int) = 0.0466] |
| Completeness to theta = 68.67° | 94.6% |
| Max. and min. transmission | 0.9475 and 0.8758 |
| Refinement method | Full-matrix least-squares on $F^2$ |
| Data/restraints/parameters | 3071/1/375 |
| Goodness-of-fit on $F^2$ | 1.001 |
| Final R indices [I > 2sigma(I)] | R1 = 0.0482, wR2 = 0.1137 |
| R indices (all data) | R1 = 0.0663, wR2 = 0.1242 |
| Absolute structure parameter | 0.0(3) |
| Extinction coefficient | 0.0008(6) |
| Largest diff. peak and hole | 0.200 and −0.218 e.Å$^{-3}$ |

TABLE 2

Atomic coordinates (×10$^4$) and equivalent isotropic displacement parameters (Å$^2$ × 10$^3$) for Compound 1. U(eq) is defined as one third of the trace of the orthogonalized U$^{ij}$ tensor.

|  | x | y | z | U(eq) |
|---|---|---|---|---|
| N(1) | 11624(2) | −530(5) | 8667(2) | 33(1) |
| C(3) | 10407(3) | 2650(6) | 8133(2) | 31(1) |
| C(4) | 10335(3) | 2115(6) | 7158(2) | 30(1) |
| C(5) | 11006(3) | 150(6) | 7013(2) | 31(1) |
| C(2) | 11034(3) | 1269(6) | 8830(2) | 32(1) |
| C(8) | 12233(3) | −3643(7) | 6701(3) | 38(1) |
| C(7) | 11610(3) | −2371(7) | 5947(3) | 37(1) |
| C(6) | 11015(3) | −530(6) | 6093(2) | 35(1) |
| C(9) | 12255(3) | −3039(7) | 7618(2) | 36(1) |
| C(11) | 9786(3) | 4549(6) | 8431(2) | 32(1) |
| C(15) | 6468(3) | 9414(6) | 7354(2) | 30(1) |
| C(19) | 7049(3) | 7025(6) | 6127(2) | 31(1) |
| C(18) | 8461(3) | 8580(6) | 8706(2) | 32(1) |
| C(13) | 8275(3) | 7448(6) | 7859(2) | 29(1) |
| C(16) | 6578(3) | 10442(6) | 8223(2) | 31(1) |
| C(17) | 7639(3) | 10044(6) | 8889(2) | 30(1) |
| C(14) | 7271(3) | 7965(6) | 7130(2) | 30(1) |
| C(23) | 5586(3) | 11841(6) | 8438(2) | 34(1) |
| C(21) | 8075(3) | 7722(7) | 5705(2) | 35(1) |
| C(22) | 5943(3) | 8034(7) | 5474(2) | 35(1) |
| C(20) | 6879(3) | 4481(7) | 6096(3) | 37(1) |
| C(24) | 4478(3) | 11888(7) | 7605(3) | 39(1) |
| C(25) | 5981(3) | 14254(7) | 8672(3) | 39(1) |
| C(26) | 5207(3) | 10760(7) | 9264(3) | 37(1) |
| N(12) | 9082(2) | 5775(5) | 7752(2) | 31(1) |
| O(11) | 9923(2) | 4910(4) | 9289(2) | 37(1) |
| O(4) | 9748(2) | 3206(4) | 6485(2) | 35(1) |
| O(17) | 7888(2) | 11078(5) | 9758(2) | 37(1) |
| C(10) | 11644(3) | −1165(6) | 7761(2) | 32(1) |

TABLE 3

Bond lengths [Å] and angles [°] for Compound 1.

| Bond | Length (° A) | Bond | Angle (deg) | Bond | Angle (deg) |
|---|---|---|---|---|---|
| N(1)—C(2) | 1.337(5) | C(2)—N(1)—C(10) | 122.0(3) | C(15)—C(16)—C(23) | 122.4(3) |
| N(1)—C(10) | 1.400(5) | C(2)—C(3)—C(4) | 119.4(3) | C(18)—C(17)—O(17) | 118.2(3) |
| C(3)—C(2) | 1.377(5) | C(2)—C(3)—C(11) | 116.6(3) | C(18)—C(17)—C(16) | 120.9(3) |
| C(3)—C(4) | 1.458(4) | C(4)—C(3)—C(11) | 123.9(3) | O(17)—C(17)—C(16) | 120.8(3) |
| C(3)—C(11) | 1.481(5) | O(4)—C(4)—C(3) | 123.8(3) | C(15)—C(14)—C(13) | 116.3(3) |
| C(4)—O(4) | 1.240(4) | O(4)—C(4)—C(5) | 120.9(3) | C(15)—C(14)—C(19) | 120.1(3) |
| C(4)—C(5) | 1.465(5) | C(3)—C(4)—C(5) | 115.3(3) | C(13)—C(14)—C(19) | 123.5(3) |
| C(5)—C(10) | 1.406(5) | C(10)—C(5)—C(6) | 117.2(3) | C(25)—C(23)—C(16) | 110.9(3) |
| C(5)—C(6) | 1.423(5) | C(10)—C(5)—C(4) | 122.2(3) | C(25)—C(23)—C(24) | 107.9(3) |
| C(8)—C(7) | 1.391(5) | C(6)—C(5)—C(4) | 120.6(3) | C(16)—C(23)—C(24) | 112.1(3) |
| C(8)—C(9) | 1.398(5) | N(1)—C(2)—C(3) | 123.4(3) | C(25)—C(23)—C(26) | 110.5(3) |
| C(7)—C(6) | 1.353(5) | C(7)—C(8)—C(9) | 120.6(4) | C(16)—C(23)—C(26) | 109.2(3) |
| C(9)—C(10) | 1.379(5) | C(6)—C(7)—C(8) | 120.3(4) | C(24)—C(23)—C(26) | 106.1(3) |
| C(11)—O(11) | 1.255(4) | C(7)—C(6)—C(5) | 121.2(3) | C(11)—N(12)—C(13) | 127.2(3) |
| C(11)—N(12) | 1.343(4) | C(10)—C(9)—C(8) | 118.7(3) | C(9)—C(10)—N(1) | 120.5(3) |
| C(15)—C(14) | 1.387(5) | O(11)—C(11)—N(12) | 123.7(3) | C(9)—C(10)—C(5) | 121.9(3) |
| C(15)—C(16) | 1.399(5) | O(11)—C(11)—C(3) | 119.4(3) | N(1)—C(10)—C(5) | 117.6(3) |
| C(19)—C(22) | 1.531(4) | N(12)—C(11)—C(3) | 117.0(3) | | |
| C(19)—C(20) | 1.534(5) | C(14)—C(15)—C(16) | 126.1(3) | | |
| C(19)—C(14) | 1.544(4) | C(22)—C(19)—C(20) | 106.8(3) | | |
| C(19)—C(21) | 1.558(5) | C(22)—C(19)—C(14) | 111.5(3) | | |
| C(18)—C(17) | 1.385(5) | C(20)—C(19)—C(14) | 112.2(3) | | |
| C(18)—C(13) | 1.390(5) | C(22)—C(19)—C(21) | 105.4(3) | | |
| C(13)—C(14) | 1.413(4) | C(20)—C(19)—C(21) | 111.3(3) | | |
| C(13)—N(12) | 1.418(4) | C(14)—C(19)—C(21) | 109.4(3) | | |
| C(16)—C(17) | 1.397(4) | C(17)—C(18)—C(13) | 122.0(3) | | |
| C(16)—C(23) | 1.539(5) | C(18)—C(13)—C(14) | 119.0(3) | | |
| C(17)—O(17) | 1.387(4) | C(18)—C(13)—N(12) | 119.4(3) | | |
| C(23)—C(25) | 1.528(5) | C(14)—C(13)—N(12) | 121.5(3) | | |
| C(23)—C(24) | 1.546(5) | C(17)—C(16)—C(15) | 115.1(3) | | |
| C(23)—C(26) | 1.548(5) | C(17)—C(16)—C(23) | 122.4(3) | | |

Symmetry Transformations Used to Generate Equivalent Atoms:

TABLE 4

Anisotropic displacement parameters (Å$^2$ × 10$^3$) for Compound 1. The anisotropic displacement factor exponent takes the form:
$-2\pi^2[h^2 a^{*2} U^{11} + \ldots + 2\,h\,k\,a^*\,b^* U^{12}]$

| | U$^{11}$ | U$^{22}$ | U$^{33}$ | U$^{23}$ | U$^{13}$ | U$^{12}$ |
|---|---|---|---|---|---|---|
| N(1) | 42(1) | 41(2) | 14(2) | 5(1) | 4(1) | 3(1) |
| C(3) | 34(2) | 40(2) | 16(2) | −1(1) | 4(1) | −4(1) |
| C(4) | 34(2) | 38(2) | 17(2) | 0(1) | 4(1) | −1(1) |
| C(5) | 34(2) | 42(2) | 17(2) | −2(1) | 6(1) | −6(1) |
| C(2) | 37(2) | 42(2) | 16(2) | 1(1) | 5(1) | 1(2) |
| C(8) | 44(2) | 41(2) | 30(2) | −4(2) | 10(1) | 5(2) |
| C(7) | 46(2) | 44(2) | 22(2) | −4(1) | 9(1) | −5(2) |
| C(6) | 41(2) | 40(2) | 23(2) | 1(2) | 9(1) | −1(2) |
| C(9) | 41(2) | 40(2) | 24(2) | 5(1) | 4(1) | 3(2) |
| C(11) | 35(2) | 41(2) | 18(2) | 1(1) | 4(1) | −4(2) |
| C(15) | 37(2) | 37(2) | 15(2) | 4(1) | 3(1) | 1(1) |
| C(19) | 38(2) | 38(2) | 14(2) | 2(1) | 5(1) | 4(1) |
| C(18) | 36(2) | 42(2) | 14(2) | 4(1) | 0(1) | 0(1) |
| C(13) | 39(2) | 34(2) | 16(2) | 2(1) | 9(1) | −3(1) |
| C(16) | 46(2) | 29(2) | 19(2) | 1(1) | 10(1) | −3(1) |
| C(17) | 43(2) | 33(2) | 14(2) | −2(1) | 7(1) | −6(1) |
| C(14) | 38(2) | 38(2) | 11(2) | 1(1) | 3(1) | −3(2) |
| C(23) | 46(2) | 40(2) | 20(2) | 2(1) | 13(1) | 3(2) |
| C(21) | 51(2) | 45(2) | 8(2) | 2(1) | 7(1) | 0(2) |
| C(22) | 44(2) | 41(2) | 16(2) | −7(1) | 1(1) | 2(2) |
| C(20) | 40(2) | 46(2) | 20(2) | −1(2) | 3(1) | 1(2) |
| C(24) | 44(2) | 49(2) | 24(2) | −2(2) | 10(1) | 5(2) |
| C(25) | 52(2) | 43(2) | 24(2) | 3(2) | 12(2) | 9(2) |
| C(26) | 48(2) | 40(2) | 24(2) | 1(2) | 14(1) | 0(2) |
| N(12) | 40(1) | 41(2) | 12(2) | 0(1) | 5(1) | 0(1) |
| O(11) | 48(1) | 47(1) | 13(2) | 1(1) | 4(1) | 5(1) |
| O(4) | 46(1) | 46(2) | 12(1) | 3(1) | 4(1) | 7(1) |

TABLE 4-continued

Anisotropic displacement parameters (Å$^2$ × 10$^3$) for Compound 1. The anisotropic displacement factor exponent takes the form:
$-2\pi^2[h^2 a^{*2} U^{11} + \ldots + 2\,h\,k\,a^*\,b^* U^{12}]$

| | U$^{11}$ | U$^{22}$ | U$^{33}$ | U$^{23}$ | U$^{13}$ | U$^{12}$ |
|---|---|---|---|---|---|---|
| O(17) | 44(1) | 45(2) | 18(1) | −6(1) | 4(1) | 4(1) |
| C(10) | 37(2) | 37(2) | 21(2) | 0(1) | 8(1) | −2(2) |

TABLE 5

Hydrogen coordinates (×10$^4$) and isotropic displacement parameters (Å$^2$ × 10$^3$) for Compound 1.

| | x | y | z | U(eq) |
|---|---|---|---|---|
| H(7) | 11560(30) | −2840(70) | 5320(30) | 35(10) |
| H(9) | 12670(30) | −3980(70) | 8120(30) | 38(10) |
| H(8) | 12680(30) | −4860(70) | 6660(30) | 36(10) |
| H(6) | 10550(30) | 350(80) | 5580(30) | 51(13) |
| H(15) | 5770(30) | 9730(70) | 6900(30) | 30(9) |
| H(18) | 9150(20) | 8310(50) | 9160(20) | 12(7) |
| H(17) | 8620(30) | 10600(60) | 10030(30) | 25(9) |
| H(20A) | 7470(30) | 3650(70) | 6460(30) | 32(10) |
| H(20B) | 6130(30) | 4320(80) | 6280(30) | 43(11) |
| H(21A) | 8840(30) | 6840(70) | 5980(30) | 40(11) |
| H(21B) | 8160(30) | 9370(80) | 5790(30) | 42(11) |
| H(22B) | 5990(30) | 9620(70) | 5480(30) | 31(9) |
| H(22A) | 5790(30) | 7200(80) | 4820(30) | 48(12) |
| H(24A) | 3800(40) | 12810(90) | 7750(30) | 57(13) |
| H(24B) | 4210(30) | 10410(70) | 7420(30) | 34(10) |
| H(25A) | 5370(30) | 15130(60) | 8770(20) | 24(9) |
| H(25B) | 6240(30) | 15040(70) | 8150(30) | 41(11) |
| H(25C) | 6690(30) | 14100(80) | 9230(30) | 44(11) |
| H(26A) | 4600(30) | 11790(60) | 9320(20) | 17(8) |
| H(26B) | 5000(30) | 9350(70) | 9090(30) | 28(9) |

TABLE 5-continued

Hydrogen coordinates (×10$^4$) and isotropic displacement parameters (Å$^2$ × 10$^3$) for Compound 1.

|       | x        | y         | z        | U(eq)   |
|-------|----------|-----------|----------|---------|
| H(1)  | 12000(30)| −1450(70) | 9140(30) | 40(11)  |
| H(2)  | 11050(40)| 1550(80)  | 9460(40) | 56(13)  |
| H(26C)| 5950(30) | 10770(80) | 9820(30) | 51(12)  |
| H(24C)| 4720(40) | 12850(100)| 7170(40) | 69(15)  |
| H(22C)| 5150(40) | 7470(70)  | 5610(30) | 42(11)  |
| H(21C)| 7820(40) | 7310(90)  | 5040(40) | 62(14)  |

TABLE 5-continued

Hydrogen coordinates (×10$^4$) and isotropic displacement parameters (Å$^2$ × 10$^3$) for Compound 1.

|       | x       | y        | z       | U(eq)  |
|-------|---------|----------|---------|--------|
| H(20C)| 6780(30)| 3790(70) | 5480(30)| 48(12) |
| H(12) | 9030(40)| 5290(90) | 7280(40)| 62(16) |

Preparation of Amorphous Form from Form B

A Buchi Spray drier was used in this method under the following conditions:

Inlet temperature set point: 130° C.
Outlet Temperature (start of run) 55° C.
Outlet temperature (end of run): 58° C.
Nitrogen pressure: 120 psi
Aspirator: 100%
Pump: 40%
Filter pressure 11 mbar
Condenser Temperature: 10° C.
Run Time 15 min
Yield 86.5%
Dried in 25° C. vacuum over for 24 hours.

4 g of Form B was dissolved in 86.4 g of acetone and 9.6 g water under the above conditions. The run time was 15 min. The product was dried under vacuum at 25° C. for over 24 hrs to produce the Amorphous Form.

Figure 11:
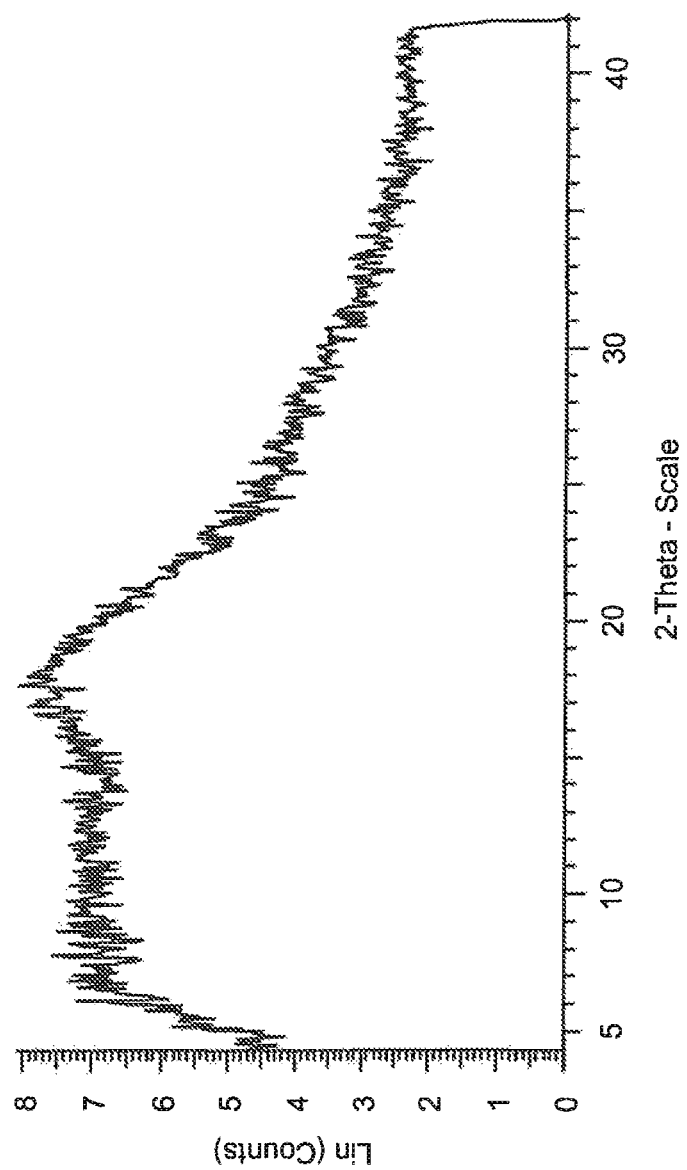
FIG. 11 is the X-Ray powder diffraction pattern of the Amorphous Form.

The XRPD spectrum of the Amorphous Form is shown in FIG. 11.

Figure 12:
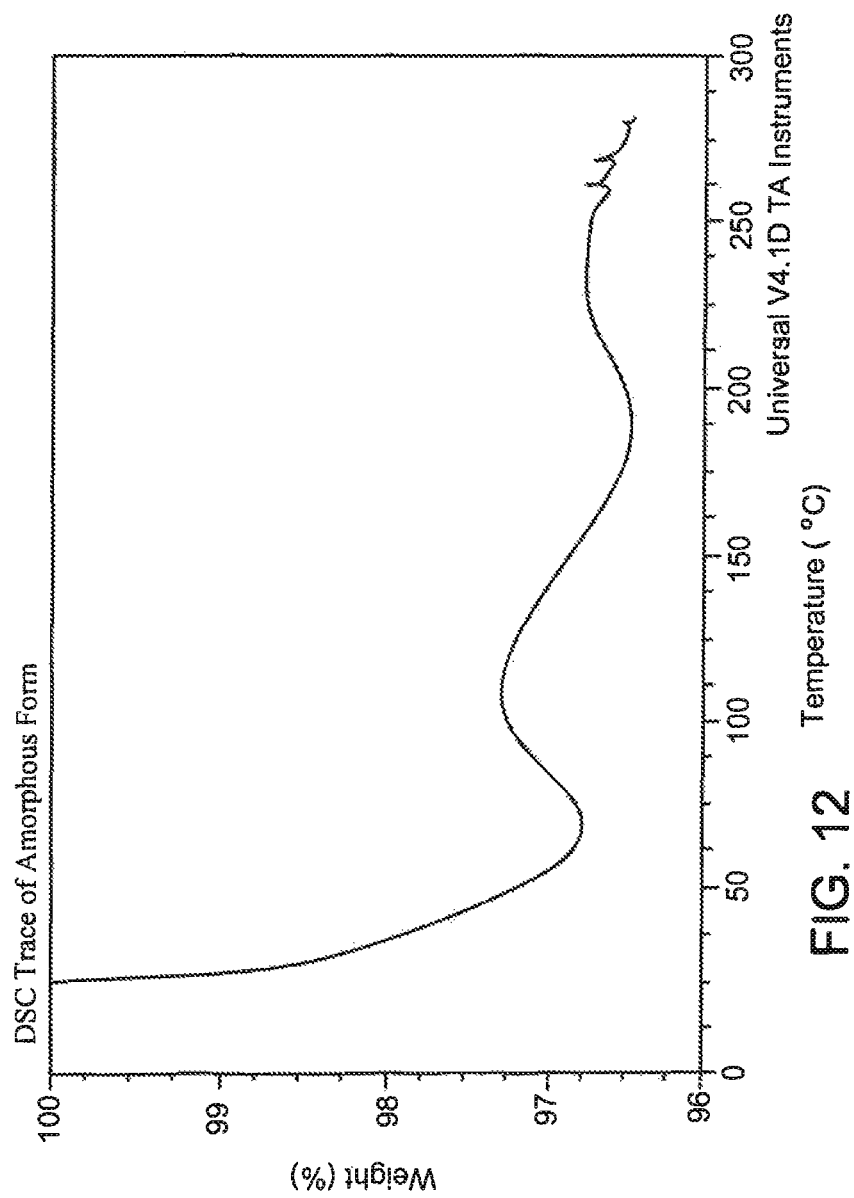
FIG. 12 is the TGA trace of the Amorphous Form.
Figure 13:
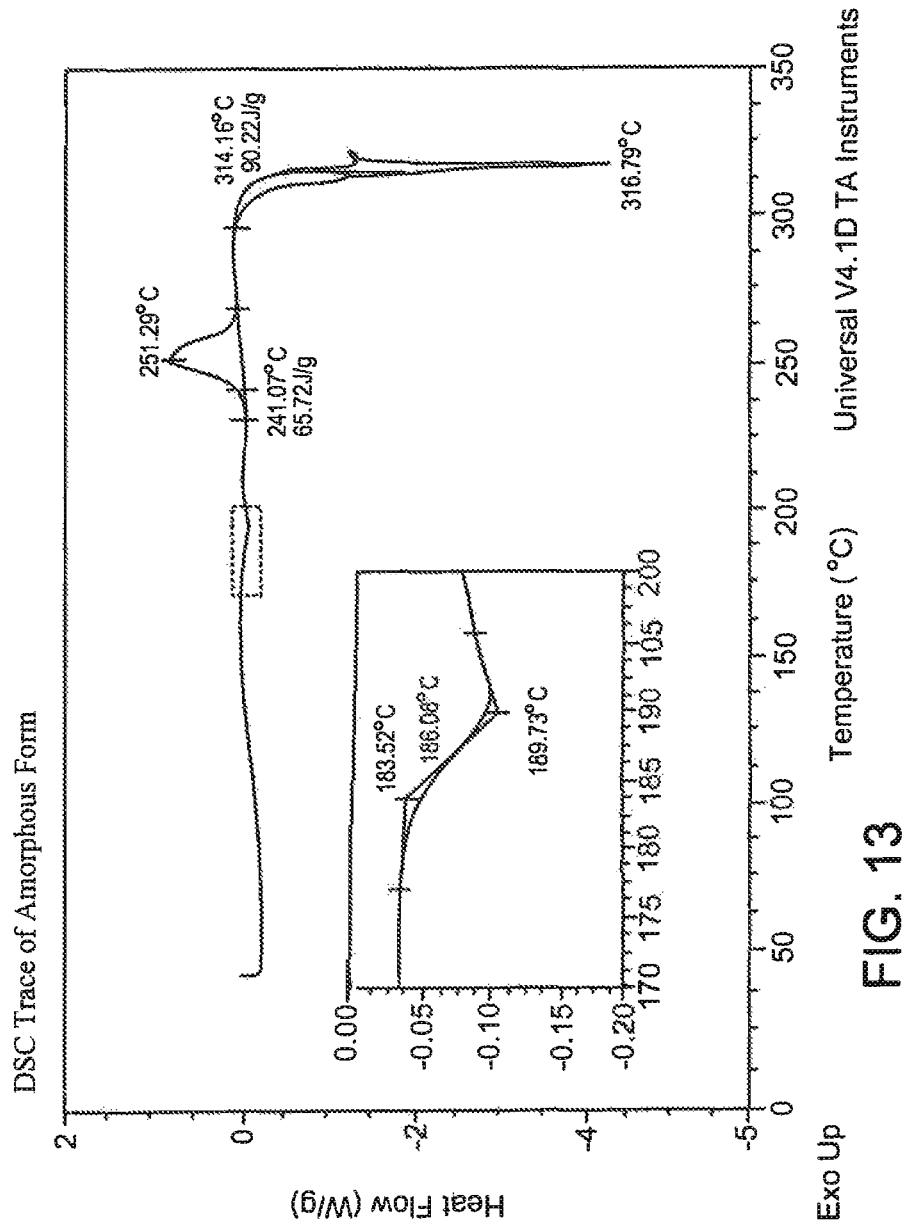
FIG. 13 is the DSC trace of the Amorphous Form.

The TGA trace for Amorphous Form is shown in FIG. 12.
The DSC trace for Amorphous Form is shown in FIG. 13.

PK and Solubility of Different Solid State Forms of Compound 1

Bioavailability of crystalline Form B, 85% amorphous Compound 1 and HPMCAS solid dispersion of Compound 1 were evaluated in rat, the results of which are provided in Table 4 below. These forms of the compound were dosed in an oral suspension with a vehicle containing 0.5% methyl cellulose/0.5% SLS/99% water. Bioavailability of various solid forms was evaluated as compared to a multicomponent IV solution of Compound 1. Bioavailability of crystalline polymorph 13 was 3-6%, compared to 61-95% for amorphous material and 109-111% for solid dispersion. In FaS-SIF, crystalline polymorph B has a measured solubility of 1.0 µg/ml, while the 85% amorphous material has a solubility of 67.4 µg/ml. The crystalline material showed 67-74% bioavailability when dosed as a PEG solution, indicating that absorption was solubility limited.

TABLE 4

| Drug Form | Vehicle | Dose (mg/kg) | AUC (ug*hr/mL) | | Tmax (h) | | % F | |
|---|---|---|---|---|---|---|---|---|
| 85% Amorphous | 0.5% MC/ 0.5% SLS | 50 | 135.5 | 27.6 | 6.0 | 0.0 | 95.0 | 20.0 |
| 85% Amorphous | 0.5% MC/ 0.5% SLS | 200 | 371.9 | 46.1 | 6.0 | 0.0 | 61.0 | 7.0 |
| Crystalline | 0.5% MC/ 0.5% SLS | 50 | 8.0 | 1.2 | 4.0 | 0.0 | 5.5 | 0.8 |
| Crystalline | 0.5% MC/ 0.5% SLS | 200 | 16.9 | 3.0 | 4.7 | 1.2 | 3.1 | 0.3 |
| Crystalline | PEG | 50 | 135.1 | 43.0 | 5.5 | 1.0 | 74.0 | 23.0 |
| Crystalline | PEG | 200 | 431.5 | 101.1 | 14.5 | 11.0 | 67.0 | 16.0 |
| Solid Dispersion | 0.5% MC/ 0.5% SLS | 25 | 90.1 | 8.1 | 6.0 | 0.0 | 111.0 | 10.0 |
| Solid Dispersion | 0.5% MC/ 0.5% SLS | 100 | 260.8 | 28.4 | 6.0 | 0.0 | 109.0 | 12.0 |

What is claimed is:

1. A crystal form of N-[2,4-bis(1,1-dimethylethyl)-5-hydroxyphenyl]-1,4-dihydro-4-oxoquinoline-3-carboxamide, having at least one peak within a 2θ value range selected from 6.0 to 6.4, 10.8 to 11.2, 16.9 to 17.3, 19.2 to 19.6, 20.9 to 21.3, 22.4 to 22.8, 26.5 to 26.9 and 27.3 to 27.7 degrees in an X-ray powder diffraction pattern obtained using Cu K alpha radiation.

2. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 8.2 to 8.6 degrees.

3. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 10.8 to 11.2 degrees.

4. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 14.6 to 15.0 degrees.

5. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 15.9 to 16.3 degrees.

6. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 16.9 to 17.3 degrees.

7. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 18.4 to 18.8 degrees.

8. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 19.2 to 19.6 degrees.

9. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 20.9 to 21.3 degrees.

10. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 22.4 to 22.8 degrees.

11. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 23.2 to 23.6 degrees.

12. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 23.7 to 24.1 degrees.

13. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 24.7 to 25.1 degrees.

14. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 25.3 to 25.7 degrees.

15. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 26.5 to 26.9 degrees.

16. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 27.3 to 27.7 degrees.

17. A pharmaceutical composition comprising the crystal form of N-[2,4-bis(1,1-dimethylethyl)-5-hydroxyphenyl]-1,4-dihydro-4-oxoquinoline-3-carboxamide according to claim 1, and a pharmaceutically acceptable adjuvant or carrier.

18. A process for preparing the crystal form of N-[2,4-bis(1,1-dimethylethyl)-5-hydroxyphenyl]-1,4-dihydro-4-oxoquinoline-3-carboxamide according to claim 1, wherein said process comprises the steps of alternatively heating and cooling a slurry of N-[2,4-bis(1,1-dimethylethyl)-5-hydroxyphenyl]-1,4-dihydro-4-oxoquinoline-3-carboxamide and acetonitrile.

19. A crystal form of N-[2,4-bis(1,1-dimethylethyl)-5-hydroxyphenyl]-1,4-dihydro-4-oxoquinoline-3-carboxamide, having a monoclinic crystal system, a $P2_1$ space grouping, and the following unit cell dimensions:
a=11.8011(7) Å α=90°
b=5.9819(3) Å β=105.110(4)°
c=14.7974(8) Å γ=90°.

20. A method of treating a CFTR mediated disease in a patient comprising the step of administering to said patient a crystal form of N-[2,4-bis(1,1-dimethylethyl)-5-hydroxyphenyl]-1,4-dihydro-4-oxoquinoline-3-carboxamide or a pharmaceutical composition comprising a crystal form of N-[2,4-bis(1,1-dimethylethyl)-5-hydroxyphenyl]-1,4-dihydro-4-oxoquinoline-3-carboxamide according to claim 1 or 19.

21. The method according to claim 20, wherein said disease is cystic fibrosis.

22. The crystal form of claim 1, wherein the crystal form of N-[2,4-bis(1,1-dimethylethyl)-5-hydroxyphenyl]-1,4-dihydro-4-oxoquinoline-3-carboxamide has a peak within a 2θ value range of 6.0 to 6.4 degrees.

23. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 7.4 to 7.8 degrees.

24. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 12.1 to 12.5 degrees.

25. The crystal form of claim 1, wherein the crystal form of N-[2,4-bis(1,1-dimethylethyl)-5-hydroxyphenyl]-1,4-dihydro-4-oxoquinoline-3-carboxamide further has a peak within a 2θ value range of 17.8 to 18.2 degrees.

26. A crystal form of N-[2,4-bis(1,1-dimethylethyl)-5-hydroxyphenyl]-1,4-dihydro-4-oxoquinoline-3-carboxamide, having an X-ray powder diffraction pattern, obtained using Cu K alpha radiation, substantially similar to FIG. 7.

* * * * *